(12) United States Patent
Barnes et al.

(10) Patent No.: US 11,721,427 B2
(45) Date of Patent: Aug. 8, 2023

(54) COMPUTATIONAL PATHOLOGY APPROACH FOR RETROSPECTIVE ANALYSIS OF TISSUE-BASED COMPANION DIAGNOSTIC DRIVEN CLINICAL TRIAL STUDIES

(71) Applicant: VENTANA MEDICAL SYSTEMS, INC., Tucson, AZ (US)

(72) Inventors: Michael Barnes, Tucson, AZ (US); Christophe Chefd'Hotel, Tucson, AZ (US); Srinivas Chukka, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 357 days.

(21) Appl. No.: 16/907,632

(22) Filed: Jun. 22, 2020

(65) Prior Publication Data
US 2020/0321102 A1 Oct. 8, 2020

Related U.S. Application Data

(63) Continuation of application No. PCT/EP2018/085308, filed on Dec. 17, 2018.
(Continued)

(51) Int. Cl.
*G06K 9/00* (2022.01)
*G16H 30/40* (2018.01)
(Continued)

(52) U.S. Cl.
CPC ........... *G16H 30/40* (2018.01); *G06T 7/0012* (2013.01); *G06V 20/695* (2022.01);
(Continued)

(58) Field of Classification Search
None
See application file for complete search history.

(56) References Cited

U.S. PATENT DOCUMENTS

| 5,650,327 A | 7/1997 | Copeland |
| 5,654,200 A | 8/1997 | Copeland |

(Continued)

FOREIGN PATENT DOCUMENTS

| WO | WO2011049608 | 4/2011 |
| WO | WO2014102130 | 7/2014 |

(Continued)

OTHER PUBLICATIONS

Ausubel, et al., Current Protocols in Molecular Biology, Greene Publishing Associates and Wiley-Intersciences Dec. 4, 2003, 388 pages.

(Continued)

*Primary Examiner* — Soo Jin Park
(74) *Attorney, Agent, or Firm* — Kilpatrick Townsend & Stockton LLP

(57) ABSTRACT

Automated systems and methods are presented for retrospectively analyzing clinical trial data. A plurality of image derived from biological samples of patients in a cohort population are accessed. Image features are computed based on the plurality of images. A diagnostic feature metric is derived based on the computed image features. A cut point value is determined by applying a statistical minimization method using the derived diagnostic feature metric and patient outcome data from the cohort population, in which the cut point value identifies a patient in the cohort population as positive or negative for a diagnostic test.

20 Claims, 7 Drawing Sheets

Related U.S. Application Data

(60) Provisional application No. 62/610,216, filed on Dec. 24, 2017.

(51) Int. Cl.

| | | |
|---|---|---|
| *G16H 50/70* | (2018.01) | |
| *G16H 50/20* | (2018.01) | |
| *G06T 7/00* | (2017.01) | |
| *G06V 20/69* | (2022.01) | |

(52) U.S. Cl.
CPC .......... *G06V 20/698* (2022.01); *G16H 50/20* (2018.01); *G16H 50/70* (2018.01)

(56) References Cited

U.S. PATENT DOCUMENTS

| | | | |
|---|---|---|---|
| 6,296,809 | B1 | 10/2001 | Richards |
| 6,352,861 | B1 | 3/2002 | Copeland |
| 6,827,901 | B2 | 12/2004 | Copeland |
| 6,943,029 | B2 | 9/2005 | Copeland |
| 7,760,927 | B2 | 7/2010 | Gholap et al. |
| 9,240,043 | B2 * | 1/2016 | Christiansen ........ G06V 20/698 |
| 2003/0211630 | A1 | 11/2003 | Richards |
| 2004/0052685 | A1 | 3/2004 | Richards |
| 2015/0347702 | A1 | 12/2015 | Chukka et al. |
| 2017/0098310 | A1 | 4/2017 | Chefd'hotel |
| 2017/0103521 | A1 | 4/2017 | Srinivas |
| 2017/0140246 | A1 | 5/2017 | Barnes |
| 2017/0154420 | A1 | 6/2017 | Barnes |
| 2017/0337596 | A1 | 11/2017 | Larkin |
| 2020/0234442 | A1 | 7/2020 | Barnes et al. |
| 2020/0321102 | A1 | 10/2020 | Barnes et al. |

FOREIGN PATENT DOCUMENTS

| | | |
|---|---|---|
| WO | WO2014140085 | 9/2014 |
| WO | WO2014195193 | 12/2014 |
| WO | WO2015113895 | 8/2015 |
| WO | WO2015124772 | 8/2015 |
| WO | WO2015181371 | 12/2015 |
| WO | WO2016075095 | 5/2016 |
| WO | WO2016075096 | 5/2016 |
| WO | 2016/087592 A1 | 6/2016 |
| WO | WO2016120442 | 8/2016 |
| WO | WO2019020556 | 1/2019 |

OTHER PUBLICATIONS

Balmer, et al. "Effects of Ursodeoxycholic Acid in Combination with Vitamin E on Adipokines and Apoptosis in Patients with Nonalcoholic Steatohepatitis" Liver International, vol. 29, No. 8, pp. 1184-1188 Sep. 1, 2009.

Chopra, et al. "Validation and Usefullness of Indian Version (CRD Pune) Health Assessment Questionaire: Drug Trials, Community Practice and Copcord Bhigwan Population Study", Indian Journal of Rheumatology, vol. 7, No. 2, pp. 74-82, Apr. 11, 2012.

Gonzalez, et al., Digital Image Processing, Third Edition, chapter 10, 2008, p. 689.

Huang, et al., "Densely Connected Convolutional Networks," Aug. 26, 2016, arXiv: 1608.06993, 9 pages.

Kong, et al., "A comprehensive framework for classification of nuclei in digital microscopy imaging: An application to diffuse gliomas," in ISBI, Mar. 2011, pp. 2128-2131.

Lawson, et al., "Solving least squares Problems", PrenticeHall, 1974, Chapter 23, 6 pages.

Long, et al., "Fully Convolutional Networks for Semantic Segmentation," Computer Vision and Pattern Recognition (CVPR), 2015 IEEE Conference, June 20015 (INSPEC Accession No. 15524435).

Pan, S. J., & Yang, Q. "A Survey on Transfer Learning" IEEE Transactions on Knowledge and Data Engineering, 22(10), Oct. 16, 2009, 1345-1359.

Parvin, Bahram, et al. "Iterative voting for inference of structural saliency and characterization of subcellular events." Image Processing, IEEE Transactions on 16.Mar. 3, 2007: 615-623.

Russakovsky, et al., "ImageNet Large Scale Visual Recognition Challenge" arXiv:1409.0575v3 Jan. 2015, 43 pages, https://doi.org/10.48550/arXiv.1409.0575.

Sambrook, et al.,"Molecular Cloning: A Laboratory Manual", Cold Spring Harbor Laboratory Press (1989), 30pages.

Veta, et al. "Automatic Nuclei Segmentation in H&E Stained Breast Cancer Histopathology Images," PLoS One. Jul. 2013; 8(7): e70221, 12 pages.

Xing, et al. "Robust Nucleus/Cell Detection and Segmentation in Digital Pathology and Microscopy Images: A Comprehensive Review," IEEE Rev Biomed Eng 9, 234-263, Jan. 2016.

Zimmermann, "Spectral Imaging and Linear Unmixing in Light Microscopy" Adv Biochem Engin/Biotechnol (2005) 95:245-265.

European Application No. EP18833184.7, received an Office Action dated Feb. 18, 2022, 10 pages.

International Application No. PCT/EP2018/085308 received an Inviitation to Pay Additional fees, dated Jun. 6, 2019, 10 pages.

Notice of Publication dated Sep. 30, 2020 in related foreign application No. 18833184.7, all pgs.

International Search Report and Written Opinion dated Jul. 24, 2019 in related foreign application No. PCT/EP2018/085308, all pgs.

International Preliminary Report on Patentability dated Jun. 30, 2020 in related foreign application No. PCT/EP2018/085308, all pgs.

Yao Jiawen, et al., "Imaging Biomarker Discovery for Lung Cancer Survival Prediction", Oct. 2, 2016 (Oct. 2, 2016),International Conference on Computer Analysis of Images and Patterns, CAIP 2017:Springer, Berlin, Heidelberg, pp. 649-657, XP04 7392556, ISBN: 978-3-642-17318-9 (retrieved on Oct. 2, 2016).

Harder, et. al., "Tissue Phenomics for Prognostic Biomarker Discovery in Low- and Intermediate-Risk Prostate Cancer", Nature Scientific Reports, vol. 8, No. 1, Mar. 13, 2018 (Mar. 13, 2018), pp. 1-19.

Fridlyand, et. al., "Considerations for the Successful Co-Development of Targeted Cancer Therapies and Companion Diagnostics", Nature Reviews Drug Discovery, Sep. 6, 2013 (Sep. 6, 2013), pp. 743-755.

Bankman, "Handbook of Medical Imaging, Processing and Analysis", Academic Press, 2000, chapter 2, all pages.

Barton, et al., "Assessment of the Contribution of the IHC4+C Score to Decision Making in Clinical Practice in Early Breast Cancer", British Journal of Cancer, 2012, pp. 1760-1765.

Cuzick, et al., "Prognostic Value of a Combined Estrogen Receptor, Progesterone Receptor, Ki-67, and Human Epidermal Growth Factor Receptor 2 Immunohistochemical Score and Comparison with the Genomic Health Recurrence Score in Early Breast Cancer", Journal of Clinical Oncology, vol. 29, No. 32, 2011, pp. 4273-4278.

Zhang, et al., "CutPointVis: An Interactive Exploration Tool for Cancer Biomarker Cutpoint Optimization", Advances in Visual Computing. ISVC 2016, Lecture Notes in Computer Science, vol. 10072. Springer, Cham., pp. 55-64.

* cited by examiner

COMPUTATIONAL PATHOLOGY APPROACH FOR RETROSPECTIVE ANALYSIS OF TISSUE-BASED COMPANION DIAGNOSTIC DRIVEN CLINICAL TRIAL STUDIES

CROSS-REFERENCES TO RELATED APPLICATIONS

The present application is a continuation of International Application PCT/EP2018/085308, entitled "Computational Pathology Approach For Retrospective Analysis Of Tissue-Based Companion Diagnostic Driven Clinical Trial Studies" and filed Dec. 17, 2018, which claims priority to U.S. Provisional Application No.: 62/610,216, filed Dec. 24, 2017. Each of these applications is hereby incorporated by reference in its entirety for all purposes.

BACKGROUND

In pharmaceutical development, one critical aspect of the process involves performing clinical trials of a proposed new pharmaceutical or medical device in preparation for regulatory approval. Such clinical trials involve usage of the proposed new pharmaceutical or medical device on a large number of patients and monitoring of results and potential side effects of such usage in each patient. Such clinical trials are done in phases and span a significant period of time. Extensive and often complex clinical trial protocols are developed that define, for example, targeted demographics, proposed medications, patient regimens, forms for collection, types of statistically relevant data, the timing or order of events within the study, often even the layout of the reporting data, or other suitable data.

The clinical trials are performed in a series of phases, known as Phase I, Phase II, and Phase III. Each phase varies in duration, the number of patients involved and purpose. Failure at any stage of Phases I, II or III of the clinical trial process effectively ends the therapy's chances for final approval.

Before entering Phase I, a sponsor needs to obtain regulatory approval. Phase I trials typically last six months and involve tens of volunteer subjects usually all of whom are located at a single investigative site. Phase I trials test the safety of the therapy. Once Phase I trials are complete and the therapy has been shown to be safe, the sponsor requests permission from the regulatory authority to proceed with further clinical tests.

Phase II trials typically last six to twelve months, involve tens to hundreds of patients and are conducted to test the effectiveness of the treatment, device or drug. A sponsor may conduct many Phase II trials, attempting to find as many uses of the therapy as possible. If the therapy appears to be effective, the sponsor requests permission from the regulatory authority to proceed with large scale trials.

For each likely use of the therapy, the sponsor conducts at least two Phase III trials. Phase III trials typically last 24 to 36 months and involve thousands of patients. Phase III trials are blinded trials, that is, a portion of the patients receive the therapy and the remaining patients receive a placebo or active control, and the identities of patients taking the trial therapy are not known to anyone until the trial is complete. Phase III trials are conducted to test the safety and effectiveness of a therapy in a large population. The Phase III trial is the first opportunity to observe infrequent adverse effects in the general population; each and every one is carefully recorded. Since the effectiveness of the therapy is tested in a blinded environment, the results are not known until after the study is complete.

A good number of clinical trials that succeed in Phase II fail in Phase III, and sometimes the reason for the failure is unknown or not fully appreciated. For example, it is believed that about 40% of cancer drugs fail in Phase III. When a clinical study that is successful in Phase II is unsuccessful in Phase III, possible reasons for failure are include (i) the Phase II data was not representative enough of the broader patient pool in Phase III; (ii) the underlying target biology and other interactions were not well understood; and (iii) the wrong patients were enrolled.

In some clinical studies, a companion diagnostic is used to select the intended patients. Companion diagnostic evaluation in done by analyzing patient tissue (which can be evaluating protein expression in tissue slides, or molecular or genomic analysis of the patient tissue, etc.) and a threshold may be selected for inclusion of the specific patient into the trial. Companion diagnostics should provide reproducible results.

SUMMARY

It is often necessary to understand the outcomes of clinical trial data. For example, and as noted above, if a Phase II clinical trial is successful but a subsequent Phase III clinical trial is not, it would be advantageous to understand why the Phase III trial was not successful. The systems and methods described herein enable the skilled artisan to retrospectively analyze clinical trial data, i.e. patient outcome data and/or collected image data corresponding to patient biological samples, and decipher unexpected clinical trial outcomes, or guide medical professionals in identifying necessary changes before further clinical trials are conducted.

Within this in mind, in one aspect of the present disclosure is an automated method for deriving a diagnostic cut point, the diagnostic cut point used to identify a patient in a cohort population as positive or negative for a particular diagnostic test comprising: (a) computing one or more image feature metrics from a plurality of images derived from biological samples of patients in the cohort population, the biological samples having at least one stain; (b) deriving a diagnostic feature metric based on the computed image feature metrics; and (c) applying a statistical minimization to derive the cut point value, the statistical minimization utilizing the derived diagnostic feature metric and patient outcome data from the cohort population. In some embodiments, the patient cohort is a Phase II and/or Phase III patient cohort. In some embodiments, the patient cohort is a Phase II placebo cohort, a Phase III placebo cohort, or both a Phase II and Phase III placebo cohort (i.e. cohorts that did not receive an experimental drug or treatment protocol). In some embodiments, the patient outcome data is a clinical endpoint. In some embodiments, the clinical endpoint is primary end point data. In some embodiments, the primary end point data is at least one of overall patient survival time, recurrence free survival, disease free survival, drug response, response duration, progression free survival, or pathological complete response. In some embodiments, the clinical endpoint is secondary endpoint data. In some embodiments, the patient outcome data for each cohort population is stored in a database.

In some embodiments, slides from the biological samples are digitized, and an image analysis algorithm is used to derive one or more image feature metrics. In some embodiments, the image analysis algorithm detects and classifies cells and/or nuclei within the input images, whereby the classification results may be utilized to generate one or more expression scores. In some embodiments, the generated expressions cores may be utilized as diagnostic feature metrics. In some embodiments, the expression score is an H-score. In some embodiments, the expression score is biomarker percent positivity. In some embodiments, the expressions core is an Allred score.

In some embodiments, the diagnostic feature metric is a combination of multiple image feature metrics or expression scores. In some embodiments, the multiple image feature metrics or expression scores are combined using a proportional hazard model. In some embodiments, the proportional hazard model is a multivariate Cox model. In some embodiments, the multiple image feature metrics or expression scores that are combined with the multivariate Cox model are pre-determined (e.g. determined by a pathologist or other medical profession, or based on diagnostic guidelines).

In some embodiments, the diagnostic feature metric is a combination of multiple image feature metrics or expression scores which are determined based on machine learning, i.e. using a classifier trained to determine those image feature metrics that best stratify patients when presented with patient outcome data and image analysis data. In some embodiments, the multiple image feature metrics or expression scores that are determined through machine learning are combined in a multivariate Cox model. In some embodiments, a classifier for machine learning is built using image data and patient outcome data from of a placebo cohort, a treatment arm cohort, or both the placebo and treatment arm cohorts. In some embodiments, the trained classifier will determine a top N number of image feature metrics out of a total M number of image feature metrics that best stratify patients based on patient outcome data presented to the classifier.

In some embodiments, the statistical minimization method is a log rank statistic minimization. In some embodiments, the method further comprises stratifying the patients into diagnostic positive and diagnostic negative groups based on the determined cut point value. In some embodiments, the method further comprises generating Kaplan-Meier response curves. In some embodiments, the method further comprises calculating hazard ratios based on the generated Kaplan-Meier response curves. In some embodiments, the method further comprises comparing the determined cut point value to a manually selected diagnostic cutoff value.

In some embodiments, the images are of biological samples stained for the detection of breast cancer biomarkers. In some embodiments, the images are of biological samples stained for the detection of non-small lung cell cancer biomarkers.

In another aspect of the present disclosure is a system which retrospectively analyzes clinical trial data, the system comprising: (i) one or more processors, and (iii) a memory coupled to the one or more processors, the memory to store computer-executable instructions that, when executed by the one or more processors, cause the one or more processors to perform operations comprising: (a) computing one or more image feature metrics from a plurality of images derived from biological samples of patients in a cohort population, the biological samples having at least one stain; (b) deriving a diagnostic feature metric based on the computed image feature metrics, and (c) applying a statistical minimization method to derive a cut point value, wherein the statistical minimization method takes into account the derived diagnostic feature metric and patient outcome data from the cohort population. In some embodiments, the patient cohort is a Phase II and/or Phase III patient cohort. In some embodiments, the patient cohort is a Phase II placebo cohort, a Phase III placebo cohort, or both a Phase II and Phase III placebo cohort (i.e. cohorts that did not receive an experimental drug or treatment protocol). In some embodiments, the patient outcome data is a primary end point data. In some embodiments, the primary end point data is at least one of overall patient survival time, recurrence free survival, drug response, or pathological complete response. In some embodiments, the statistical minimization method is a log rank statistic minimization.

In some embodiments, the diagnostic feature metric is derived through multivariate Cox modeling taking into account multiple computed image feature metrics. In some embodiments, the multiple computed image feature metrics for Cox modeling are predetermined (e.g. multiple expression scores as determined by a pathologist).

In some embodiments, machine learning is used to determine those computed image feature metrics that most accurately may be used to stratify patient cohorts. In some embodiments, the image feature metrics that most accurately may be used to stratify patient cohorts are fed to a multivariate Cox model to provide the diagnostic feature metric.

In some embodiments, the system further comprises instructions for stratifying the patients into diagnostic positive and diagnostic negative groups based on the determined cut point value. In some embodiments, the system further comprises instructions for generating Kaplan-Meier response curves. In some embodiments, the system further comprises instructions for calculating hazard ratios based on the generated response curves. In some embodiments, the system further comprises instructions for comparing the determined cut point value to a manually selected diagnostic cutoff value.

In another aspect of the present disclosure is a non-transitory computer-readable medium including instructions for retrospectively analyzing clinical trial data comprising: (a) computing one or more image feature metrics from a plurality of images derived from biological samples of patients in a cohort population, the biological samples having at least one stain; (b) deriving a diagnostic feature metric based on the computed image feature metrics, and (c) applying a statistical minimization method to derive a cut point value, wherein the statistical minimization method takes into account the derived diagnostic feature metric and patient outcome data from the cohort population. In some embodiments, the patient cohort is a Phase II and/or Phase III patient cohort. In some embodiments, the patient cohort is a Phase II placebo cohort, a Phase III placebo cohort, or both a Phase II and Phase III placebo cohort (i.e. cohorts that did not receive an experimental drug or treatment protocol). In some embodiments, the patient outcome data is a primary end point data. In some embodiments, the primary end point data is at least one of overall patient survival time, recurrence free survival, drug response, or pathological complete response. In some embodiments, the statistical minimization method is a log rank statistic minimization.

In some embodiments, the diagnostic feature metric is derived from multivariate Cox modeling. In some embodiments, the multivariate Cox model is built using multiple computed image feature metrics. In some embodiments, the multiple computed image feature metrics are predetermined. In some embodiments, the multiple computed image feature metrics are determined through machine learning.

In some embodiments, the multivariate Cox model is built from image feature metrics determined by machine learning to best stratify patient cohorts. In some embodiments, patient output data and image analysis data are supplied to a classifier such that those image feature metrics that best correlate with patient outcome data may be determined.

In another aspect of the present disclosure is a method of comparing sets of data from two patient populations comprising: (a) computing one or more image feature metrics from a plurality of images of biological samples derived from a first patient population; (b) combining the computed one or more image feature metrics from the first patient population with tissue analysis data corresponding to the biological samples derived from the first patient population to provide tissue feature data for the first patient population; (c) computing a first patient population correlation matrix based (i) on the tissue feature data for the first patient population, and (ii) clinical attributes of the first patient population; (d) computing one or more image feature metrics from a plurality of images of biological samples derived from a second patient population; (e) combining the computed one or more image feature metrics from the second patient population with tissue analysis data corresponding to the biological samples derived from the second patient population to provide tissue feature data for the second patient population; (f) computing a second patient population correlation matrix based (i) on the tissue feature data for the second patient population, and (ii) clinical attributes of the second patient population; and (g) determining whether the tissue feature data for the first patient population is similar to the tissue feature data for the second patient population by comparing the first and second patient population correlation matrices.

In some embodiments, the tissue analysis data includes molecular and/or genomic features. In some embodiments, the clinical attributes are selected from the group consisting of age, weight, immune response, sex, and ethnicity. In some embodiments, at least 50 tissue features are collected for each patient population.

In some embodiments, the first patient population is a Phase II patient cohort, while the second patient population is a Phase III patient cohort. In some embodiments, the first patient population is a Phase II placebo cohort, while the second patient population is a Phase III placebo cohort. In some embodiments, the first patient population is a Phase II test arm cohort, while the second patient population is a Phase III placebo cohort. In some embodiments, the first patient population is a Phase II test arm cohort, while the second patient population is a Phase III test arm cohort. In some embodiments, the first patient population is a Phase II placebo cohort, while the second patient population is a Phase II test arm cohort. In some embodiments, the first patient population is data collected pre-treatment; while the second patient population is data collected from the same patients post-treatment.

In another aspect of the present disclosure is a method of comparing sets of data from two patient populations comprising: (a) computing one or more image feature metrics from a plurality of images of biological samples derived from a first patient population; (b) combining the computed one or more image feature metrics from the first patient population with tissue analysis data corresponding to the biological samples derived from the first patient population to provide tissue feature data for the first patient population; (c) computing distributions of individual tissue features from the first patient population; (d) computing one or more image feature metrics from a plurality of images of biological samples derived from a second patient population; (e) combining the computed one or more image feature metrics from the second patient population with tissue analysis data corresponding to the biological samples derived from the second patient population to provide tissue feature data for the second patient population; (f) computing distributions of individual tissue features for the second patient population; and (g) determining whether the tissue feature data for the first patient population is similar to the tissue feature data for the second patient population by comparing the computed distributions of individual tissue features from the first and second patient populations.

DETAILED DESCRIPTION

Figure 1:
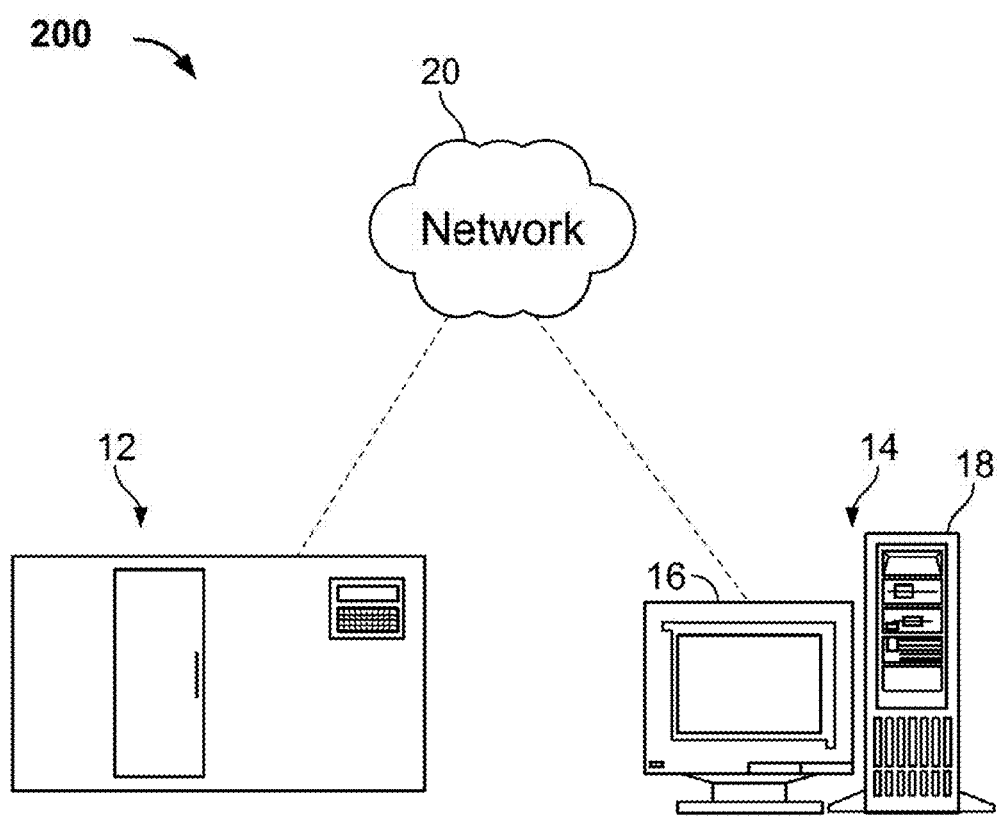
FIG. 1 illustrates a representative digital pathology system including an image acquisition device and a computer system.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary. The term "amplification," as used herein, refers to a process of multiplying an original quantity of a nucleic acid template in order to obtain greater quantities of the original nucleic acid.

As used herein, the term "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the terms "biomarker" or "marker" refer to a measurable indicator of some biological state or condition. In particular, a biomarker may be a protein or peptide, e.g. a surface protein, that can be specifically stained and which is indicative of a biological feature of the cell, e.g. the cell type or the physiological state of the cell. An immune cell marker is a biomarker that is selectively indicative of a feature that relates to an immune response of a mammal. A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the phrase "Cox proportional hazard model" refers to a model which is expressed mathematically as $h(x,t)=h_0(t) \times \exp\{b_1 x_1 + b_2 x_2 + \ldots + b_p x_p\}$ wherein $h(x,t)$ is the expected hazard at time t and $b_1, b_2 \ldots b_p$ are constants extrapolated for each of the independent variables.

As used herein, the terms "cutoff" or "clinical cutoff" refer, in the context of treatment with a therapeutic product, a value set by taking a risk-benefit balance of the therapeutic product into account. For example, and in the context of a companion diagnostic measuring the presence or absence of a particular biomarker, subjects are considered to be biomarker-positive if they are above a predetermined cutoff value; and biomarker-negative if they are below a predetermined cutoff value. Treatment decisions will be made with respect to the groups divided by such a clinical cut-off.

As used herein, the term "companion diagnostic" refers to a medical device or assay which provides information that is essential for the safe and effective use of a corresponding drug or biological product. The test helps a health care professional determine whether a particular therapeutic product's benefits to patients will outweigh any potential serious side effects or risks. In some embodiments, the clinical performance of the companion diagnostic is the ability of the test developed for a predictive biomarker (the companion diagnostic) to distinguish treatment responders from non-responders. Companion diagnostics can: (i) identify patients who are most likely to benefit from a particular therapeutic product; (ii) identify patients likely to be at increased risk for serious side effects as a result of treatment with a particular therapeutic product; and/or (iii) monitor response to treatment with a particular therapeutic product for the purpose of adjusting treatment to achieve improved safety or effectiveness. The clinical performance of the companion diagnostic not only directly affects the number of patients who are potentially eligible for treatment but also affects the net benefit enrichment achieved, as patients who are selected by the companion diagnostic and are non-responders also receive treatment, thereby reducing the observed average response. As such, if the diagnostic test is inaccurate, then the treatment decision based on that test may not be optimal.

As used herein, the terms "endpoints" or "outcomes" describe and define the goal(s) of a clinical study. Examples of endpoints (which vary depending on the type and phase of trial) include overall survival, toxicity, tumor response, patient survival or quality of life.

As used herein, the term "image data" encompasses raw image data acquired from the biological tissue sample, such as by means of an optical sensor or sensor array, or pre-processed image data. In particular, the image data may comprise a pixel matrix.

As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection).

As used herein, the terms "placebo" or "control" refer to a group of patients that receive an inactive substance while the drug being evaluated is given to another group: designed to compare efficacy of the drug with 'no' treatment. Placebo-controlled trials are rarely used for cancer treatments, where a new treatment is more likely to be compared with the existing standard-of-care treatment.

As used herein, the term "stratification" refers to a way of grouping subsets of patients and is used in randomized trials when factors that can influence the intervention's success are known. For example, participants whose cancer has spread from the original tumor site can be separated, or stratified, from those whose cancer has not spread, since it might be expected that these patients have more advanced and less advanced disease respectively and could respond differently to treatment interventions.

Overview

The present disclosure provides automated systems and methods for retrospectively analyzing clinical trial data to disambiguate and better understand why a clinical trial was successful or unsuccessful. Indeed, utilization of the systems and methods described herein allows for the skilled artisan to better understand why, for instance, a successful Phase II study was not as successful during Phase III trials or why the Phase III trial outright failed. For example, by using the systems and methods described herein, the skilled artisan will be able to appreciate whether the Phase II data was representative enough of the broader patient pool introducing during Phase III trials. Likewise, the skilled artisan will be able to make a determination of whether the appropriate patients were enrolled within the clinical study, based on the choice of the tissue-based companion diagnostic, or whether the thresholds for the companion-diagnostic were appropriately selected.

In view of this, the present disclosure provides, in some embodiments, methods for determining an optimal cut point based on image feature data and patient outcome data. The determination of the optimal cut point may allow for the generation of drug response curves, such that generated drug response curves may yield hazard ratios. Likewise, the determination of the optimal cut point may allow for the comparison with the predictive cut point for the clinical trial and/or a comparison of patient stratification based on the optimal and predictive cut points. These and other features of the present disclosure will be described herein.

Digital Pathology Systems

Figure 2:
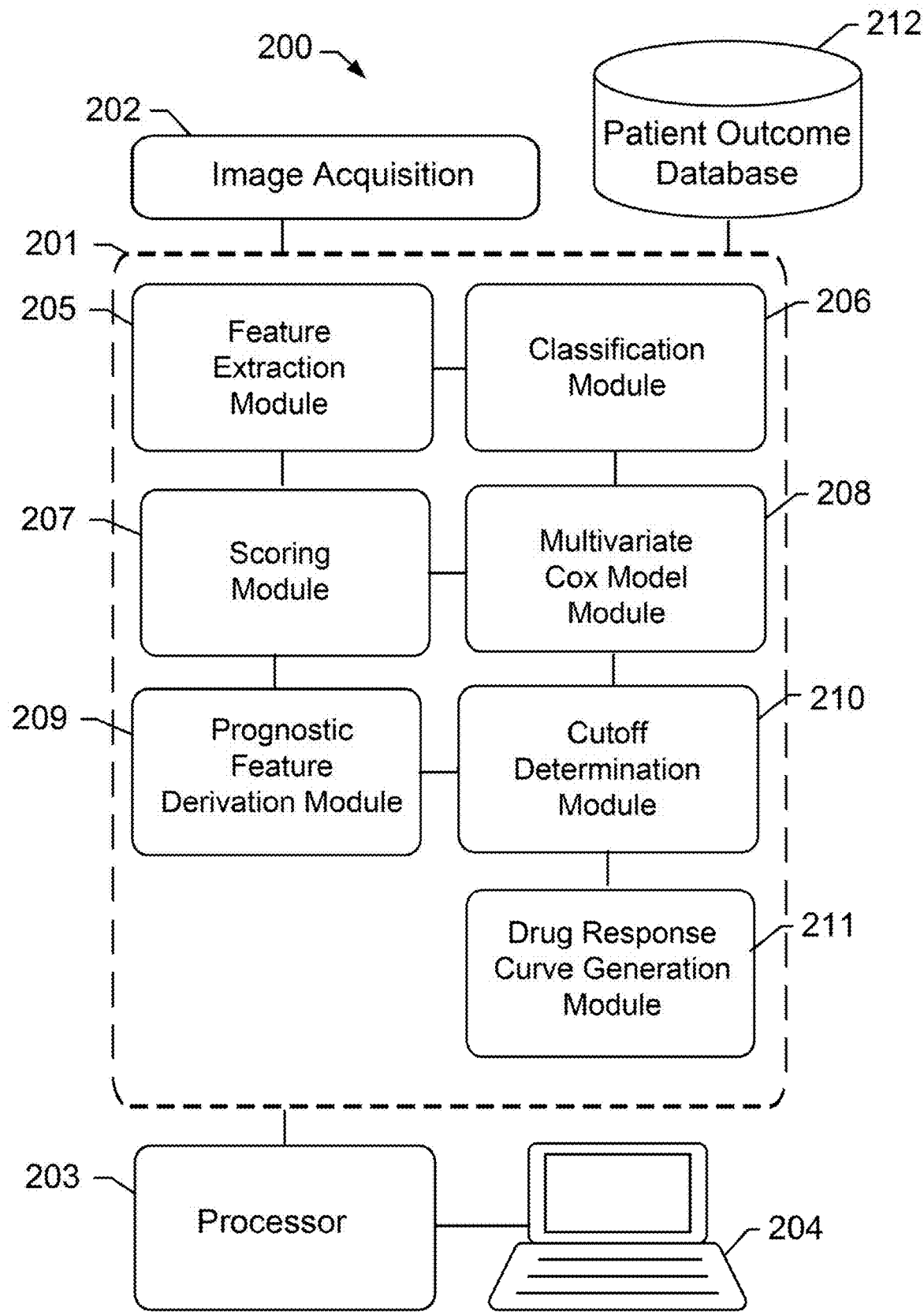
FIG. 2 sets forth various modules that can be utilized in a digital pathology system or within a digital pathology workflow.

A digital pathology system 200 for imaging and analyzing specimens is illustrated in FIGS. 1 and 2. The digital pathology system 200 may comprise an imaging apparatus 12 (e.g. an apparatus having means for scanning a specimen-bearing microscope slide) and a computer system 14, whereby the imaging apparatus 12 and computer system may be communicatively coupled together (e.g. directly, or indirectly over a network 20). The computer system 14 can include a desktop computer, a laptop computer, a tablet, or the like, digital electronic circuitry, firmware, hardware, memory 201, a computer storage medium (240), a computer program or set of instructions (e.g. where the program is stored within the memory or storage medium), one or more processors (209) (including a programmed processor), and any other hardware, software, or firmware modules or combinations thereof (such as described further herein). For example, the computing system 14 illustrated in FIG. 1 may comprise a computer with a display device 16 and an enclosure 18. The computer system can store digital images in binary form (locally, such as in a memory, on a server, or another network connected device). The digital images can also be divided into a matrix of pixels. The pixels can include a digital value of one or more bits, defined by the bit depth. The skilled artisan will appreciate that other computer devices or systems may be utilized and that the computer systems described herein may be communicatively coupled to additional components, e.g. specimen analyzers, microscopes, other imaging systems, automated slide preparation equipment, etc. Some of these additional components and the various computers, networks, etc. that may be utilized are described further herein.

In general, the imaging apparatus 12 (or other image source including pre-scanned images stored in a memory) can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging apparatus 12 is a brightfield imaging system, a multispectral imaging (MSI) system or a fluorescent microscopy system. The digitized tissue data may be generated, for example, by an image scanning system, such as a VENTANA iScan HT scanner by VENTANA MEDICAL SYSTEMS, Inc. (Tucson, Ariz.) or other suitable imaging equipment. Additional imaging devices and systems are described further herein. The skilled artisan will appreciate that the digital color image acquired by the imaging apparatus 12 is conventionally composed of elementary color pixels. Each colored pixel can be coded over three digital components, each comprising the same number of bits, each component corresponding to a primary color, generally red, green or blue, also denoted by the term "RGB" components.

FIG. 2 provides an overview of the various modules utilized within the presently disclosed digital pathology system. In some embodiments, the digital pathology system 200 employs a computer device or computer-implemented method having one or more processors 203 and at least one memory 201, the at least one memory 201 storing non-transitory computer-readable instructions for execution by the one or more processors to cause the one or more processors to execute instructions (or stored data) in one or more modules (e.g. modules 202, and 205 through 211). Alternatively, the instructions may be stored in a non-transitory computer-readable medium (201) or computer-usable medium.

Figure 3:
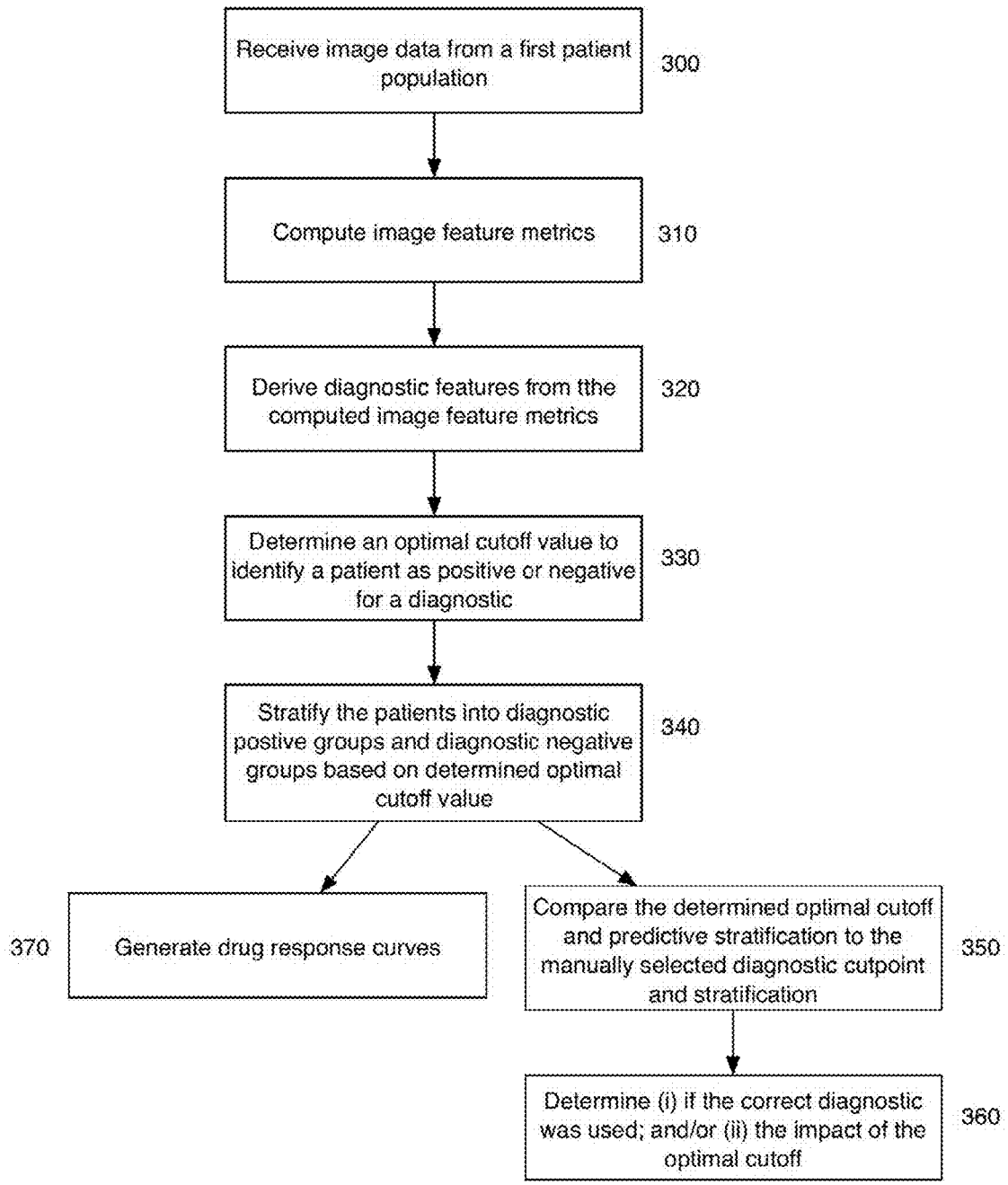
FIG. 3 sets forth a flowchart illustrating the steps of deriving a cut point and using the derived cut point in generating drug response curves and/or analyzing clinical trial data.

With reference to FIGS. 2 and 3, the present disclosure provides a system and method of retrospectively analyzing clinical trial data, the system and method comprising (a) an image acquisition module 202 to generate or receive simplex or multiplex images, e.g. acquired images of a biological sample stained with one or more stains (step 300); (b) running feature extraction module 205 to derive image feature metrics from the input images (step 310); (c) running an optional classification module 206 to classify cells and/or nucleic within the input images (d) running an optional scoring module 207 to score image data using the derived image feature metrics and/or classification results; (e) running an optional multivariate Cox model module 208 to derive a diagnostic feature based on a weighted combination of multiple image feature metrics or expressions; (f) running an optional prognostic feature derivation module 209 to determine the most relevant features coinciding within patient outcome data; (g) running a cutoff determination module 210 to determine a cut point (step 330), which facilitates the stratification of patients into diagnostic positive and negative groups (step 330) and enables statistical comparisons to be made (steps 350 and 360); and (h) running an optional drug response curve generation module 211 to compute drug response curves for different patient populations (step 370). The skilled artisan will also appreciate that additional modules may be incorporated into the workflow. As will be described in more detail here, in some embodiments, an image processing module may be run to apply certain filters to the acquired images or to identify certain histological and/or morphological structures or features within the tissue samples. Likewise, a region of interest selection module may be utilized to select a particular portion of an image for analysis.

FIG. 3 sets forth a flowchart which provides a general overview of the methods of the presently disclosed workflow. In general, the method includes receiving image data from a first patient population (step 300); deriving a diagnostic feature metrics from the received image data (step 320) by extracting image feature metrics from input images (step 310); and determining an optimal cutoff value to identify a patient as positive or negative for a diagnostic (step 330), the optical cutoff being determined using derived diagnostic feature metrics and patient outcome data (such as outcome data stored in database 212). In some embodiments, the method further comprises the step of stratifying patients into diagnostic positive and negative groups (step 340) and comparing the determined optimal cutoff and predictive stratification to the manually selected diagnostic cut point and manually selected stratification (step 350). In some embodiments, the method further comprises the step of determining whether the correct companion diagnostic was used and/or the impact of the optimal cutoff (step 360). In some embodiments, the method further comprises the step of generating drug response curves (step 370).

Patient Outcome Database

With reference to FIG. 2, the digital pathology systems of the present disclosure may include a patient outcome database 212 which serves as a repository of data pertaining to clinical trials for particular patient cohorts under study. Indeed, the database 212 may facilitate the storage of any primary and secondary endpoint data, as well as any associated patient data (e.g. patient name or identification, age, sex, weight, ethnicity, tumor size, tumor type, genetic information, pathological finds, etc.), whereby the data stored therein may be retrieved by the digital pathology system 200 and be used in further downstream processing (e.g. statistical analyses).

As the skilled artisan will appreciate, the aim of a clinical trial is to measure key outcomes or endpoints and to test the clinical efficacy and tolerability of the treatment in a particular disease. In some embodiments, trial will usually specify a primary endpoint. This is the most important endpoint of the trial and, if met, means a positive result for the trial and the treatment. In general, in a clinical research trial, a clinical endpoint generally refers to occurrence of a disease, symptom, sign or laboratory abnormality that constitutes one of the target outcomes of the trial. A clinical trial will usually define or specify a primary endpoint as a measure that will be considered success of the therapy under trial (e.g. in justifying a marketing approval). The clinical trial protocol provides the design for the study conduct and sets out the endpoints of the study up-front. There is clear guidance on how and when to measure and evaluate the study endpoints.

In some embodiments, the primary endpoint might be a statistically significant improvement in overall survival ("OS"), i.e. the time from randomization until death from any cause. Overall survival is defined as the time from randomization until death from any cause and is documented by the date of death. Overall survival can be measured in two ways: either as median overall survival, which is a duration of time at which 50% of patients in the trial are alive, or as a percentage of patients alive at different time points during the trial, which may be measured at 1, 2, or 5 years. Median overall survival is often used as a primary or co-primary endpoint. In some cases, post-marketing studies will continue in order to capture overall survival after initial efficacy is validated.

In some embodiments, overall survival is reported as a five-year survival rate, i.e. percentage of patients alive five years after diagnosis or treatment. The overall survival rates reported after diagnosis of different diseases can vary, since some cancers have a better outlook (survival rate) than others. The effect of a treatment on overall survival should be viewed relative to the background or expected overall survival for a given cancer.

A trial might also define one or more secondary endpoints. Such secondary endpoints include, without limitation, progression-free-survival (PFS) (i.e. the time from randomization until disease progression or death); time to progression (TTP) (i.e. the time from randomization until objective tumor progression; does not include deaths); time to treatment failure (TTF) (i.e. time from randomization to discontinuation of treatment for any reason, including disease progression, treatment toxicity, and death); and event-free survival (EFS) (i.e. time from randomization to disease progression, death, or discontinuation of treatment for any reason (e.g., toxicity, patient preference, or initiation of a new treatment without documented progression)). As a specific example, PFS-6 is the rate, or proportion of patients given a treatment that survive without their disease worsening at six months after treatment began.

Response rate (RR) measures tumor size, usually using a scan or X-ray. It gives an indication of whether the tumor is responding to a treatment—if the tumor size has shrunk, it is deemed that there has been a "response". There are different ways of determining response rate and the internationally recognized RECIST (Response Evaluation Criteria In Solid Tumors) guidelines are often used in clinical trials.

The trial design is not complete when the trial population, treatment and endpoints have been identified and defined. In phase III and some phase II trials in cancer, the patient population may be randomized (randomly allocated to receive one or other of the alternative treatments being studied) and stratified (partitioned by a factor other than the treatment, often to ensure that equal numbers of participants with a characteristic thought to affect prognosis or response to the intervention will be allocated to each comparison group). The gold standard in clinical research is a scientifically rigorous, randomized, well controlled trial.

Image Acquisition Module

With reference to FIG. 2, the digital pathology system 200 runs an image acquisition module 202 to capture images or image data of a biological sample having one or more stains (i.e. the images may be simplex images or multiplex images). In some embodiments, the images captured are stored in memory 201. In some embodiments, the image acquisition module 202 is a database or memory comprising previously digitized and stored images from patient biological samples stained with one or more stains (or a plurality of digital images for each patient in a cohort of patients). In some embodiments, the images received or acquired are RGB images or multispectral images. In some embodiments, in place of the captured raw images, any set of optional pre-processed images from the captured raw images can be used, either as an independent input images or in combination with the captured raw images. Accordingly, similar pre-processing step can be used when applying the trained network to an unlabeled image, as described herein.

In some embodiments, image data is received from a specific patient population undergoing a clinical trial. For example, image data may be received for a Phase II cohort and/or a Phase II cohort that received placebo.

The images or image data (used interchangeably herein) may be acquired using the imaging apparatus 12, such as in real-time. In some embodiments, the images are acquired from a microscope or other instrument capable of capturing image data of a specimen-bearing microscope slide, as noted herein. In some embodiments, the images are acquired using a 2D scanner, such as one capable of scanning image tiles, or a line scanner capable of scanning the image in a line-by-line manner, such as the VENTANA DP 200 scanner. Alternatively, the images may be images that have been previously acquired (e.g. scanned) and stored in a memory 201 (or, for that matter, retrieved from a server via network 20).

In some embodiments, the images (again, either simplex or multiplex images) received as input are derived from serial tissue sections, i.e. serial sections derived from the same xenograft tissue block. In general, the at least two images received as input each comprise signals corresponding to a stain (including chromogens, fluorophores, quantum dots, etc.). In some embodiments, the images have been stained with a least one primary stain (hematoxylin or eosin) and/or have been stained in at least one of an IHC assay or ISH assay for the identification of a specific biomarker (referred to herein as a "biomarker" image). In some embodiments, multiple images are received for each patient in a clinical study, and at least one of the images has been stained with both hematoxylin and eosin (referred to herein as an "H&E image"), while another one of the images has been stained in at least one of an IHC assay or ISH assay for the identification of a specific biomarker. In some embodiments, the input images may be multiplex images, i.e. stained for multiple, different markers in a multiplex assay according to methods known to those of ordinary skill in the art.

A typical biological sample is processed in a staining/assay platform that applies a stain to the sample. In some embodiments, specimen processing apparatus is an automated apparatus, such as the BENCHMARK XT instrument, the SYMPHONY instrument, the BENCHMARK ULTRA instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety for all purposes. Alternatively, specimens can be manually processed.

Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH. Other commercial products on the market suitable for use as the staining/assay platform, one example being the Discovery™ product of Ventana Medical Systems, Inc. (Tucson, Ariz.).

The camera platform may also include a bright field microscope, one example being the VENTANA iScan HT product of Ventana Medical Systems, Inc., or any microscope having one or more objective lenses and a digital imager, as well as a set of spectral filters. Other techniques for capturing images at different wavelengths may be used. Further camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure.

As the skilled artisan will appreciate, a tissue sample may be stained for different types of nuclei and/or cell membrane biomarkers. Methods for staining tissue structures and guidance in the choice of stains appropriate for various purposes are discussed, for example, in "Sambrook et al., Molecular Cloning: A Laboratory Manual, Cold Spring Harbor Laboratory Press (1989)" and "Ausubel et al., Current Protocols in Molecular Biology, Greene Publishing Associates and Wiley-Intersciences (1987)," the disclosures of which are incorporated herein by reference in its entirety for all purposes.

By way of one non-limiting example, and in the context of detecting breast cancer, in some embodiments the tissue sample is stained in an IHC assay for the presence of one or biomarkers including an estrogen receptor marker, a progesterone receptor marker, a Ki-67 marker, or a HER2 marker. As such, in some embodiments, the biomarker image used as an input is an IHC image which comprises signals (the signals corresponding to stains which may be, for example, chromogenic or fluorescent) corresponding to a presence of at least one of an estrogen receptor (ER) marker, a progesterone receptor (PR) marker, a Ki-67 marker, or a HER2 marker. In some embodiments, the sample can be analyzed to detect or measure the presence of ER, HER2, Ki-67 and PR proteins in the sample, for example a qualitative or quantitative measurement. In some embodiments, the expression patterns of ER, HER2, Ki-67 and PR proteins can also be used to determine the heterogeneity of the protein expression, such as between different tumor or cell clusters as described further herein. In some examples, the antibodies for ER, PR, HER2 and Ki-67 are obtained from Ventana Medical Systems, Inc. (Tucson, Ariz.). However, one skilled in the art will appreciate that other antibodies that can be used in the methods and kits provided herein are commercially available from other sources, such as: Novus Biologicals (Littleton, Colo.), Santa Cruz biotechnology, Inc. (Santa Cruz, Calif.), Abeam (Cambridge, Mass.), and Invitrogen (Carlsbad, Calif.).

By way of another non-limiting example, and in the context of detecting non-small cell lung cancer, in some embodiments the tissue sample is stained in an IHC assay for the presence of one or biomarkers including a PD-L1 biomarker. As such, in some embodiments, the biomarker image used as an input is an IHC image which comprises signals corresponding to a presence of a PD-L1 marker, CD3 marker and CD8 marker.

In some embodiments, the input images are optionally masked with a tissue masking module as described herein. In some embodiments, the input images are masked such that only tissue regions are present in the images. In some embodiments, a tissue region mask is generated to mask non-tissue regions from tissue regions. In some embodiments, a tissue region mask may be created by identifying the tissue regions and excluding the background regions (e.g. regions of a whole slide image corresponding to glass with no sample, such as where there exists only white light from the imaging source). The skilled artisan will appreciate that in addition to masking non-tissue regions from tissue regions, the tissue masking module may also mask other areas of interest as needed, such as a portion of a tissue identified as belonging to a certain tissue type or belonging to a suspected tumor region. In some embodiments, a segmentation technique is used to generate the tissue region masked images by masking tissue regions from non-tissue regions in the input images. Suitable segmentation techniques are as such known from the prior art, (cf. Digital Image Processing, Third Edition, Rafael C. Gonzalez, Richard E. Woods, chapter 10, page 689 and Handbook of Medical Imaging, Processing and Analysis, Isaac N. Bankman Academic Press, 2000, chapter 2). In some embodiments, an image segmentation technique is utilized to distinguish between the digitized tissue data and the slide in the image, the tissue corresponding to the foreground and the slide corresponding to the background. In some embodiments, the component computes the Area of Interest (AoI) in a whole slide image in order to detect all tissue regions in the AoI while limiting the amount of background non-tissue area that is analyzed. A wide range of image segmentation techniques (e.g., HSV color-based image segmentation, Lab image segmentation, mean-shift color image segmentation, region growing, level set methods, fast marching methods, etc.) can be used to determine, for example, boundaries of the tissue data and non-tissue or background data. Based at least in part on the segmentation, the component can also generate a tissue foreground mask that can be used to identify those portions of the digitized slide data that correspond to the tissue data. Alternatively, the component can generate a background mask used to identify those portions of the digitized slide date that do not correspond to the tissue data.

This identification may be enabled by image analysis operations such as edge detection, etc. A tissue region mask may be used to remove the non-tissue background noise in the image, for example the non-tissue regions. In some embodiments, the generation of the tissue region mask comprises one or more of the following operations (but not limited to the following operations): computing the luminance of the low resolution input image, producing a luminance image, applying a standard deviation filter to the luminance image, producing a filtered luminance image, and applying a threshold to filtered luminance image, such that pixels with a luminance above a given threshold are set to one, and pixels below the threshold are set to zero, producing the tissue region mask. Additional information and examples relating to the generation of tissue region masks is disclosed in PCT/EP/2015/062015, entitled "An Image Processing Method and System for Analyzing a Multi-Channel Image Obtained from a Biological Tissue Sample Being Stained by Multiple Stains," the disclosure of which is hereby incorporated by reference herein in its entirety for all purposes.

Figure 4:
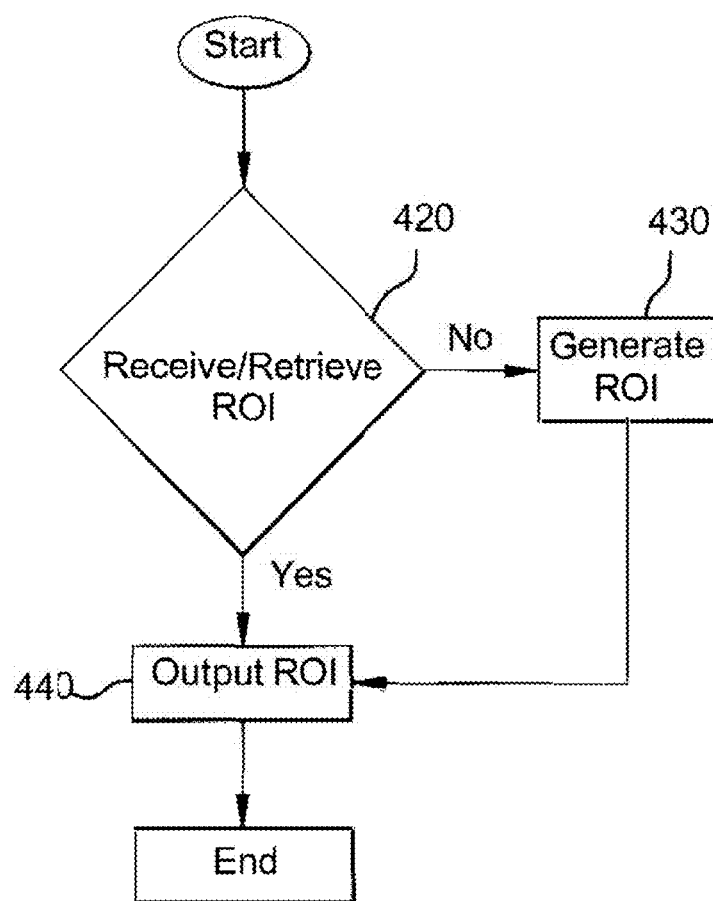
FIG. 4 provides a flow chart illustrating the steps of region selection.

In some embodiments, a region of interest identification module may be used to select a portion of the biological sample for which an image or for which image data should be acquired. FIG. 4 provides a flow chart illustrating the steps of region selection. In step 420, the region selection module receives an identified region of interest or field of view. In some embodiments, the region of interest is identified by a user of a system of the present disclosure, or another system communicatively coupled to a system of the present disclosure. Alternatively, and in other embodiments, the region selection module retrieves a location or identification of a region or interest from a storage/memory. In some embodiments, as shown in step 430, the region selection module automatically generates a FOV or ROI, for example, via methods described in PCT/EP2015/062015, the disclosure of which is hereby incorporated by reference herein in its entirety for all purposes. In some embodiments, the region of interest is automatically determined by the system based on some predetermined criteria or characteristics that are in or of the image (e.g. for a biological sample stained with more than two stains, identifying an area of the image that comprises just two stains). In step 440, the region selection module outputs the ROI.

Image Analysis

Following the receipt of image data from a patient population (e.g. a Phase II cohort receiving a placebo) or from multiple patient populations (e.g. Phase II and Phase III cohorts receiving a placebo), the image data is analyzed. Automated image analysis is utilized such that a diagnostic feature metric, derived at least from computed image feature metrics, may be provided for downstream processing. In some embodiments, the diagnostic feature metric is selected from one of (i) an expression score; (ii) a Cox hazard ratio derived from multiple, pre-selected image feature metrics and/or expression scores; and (iii) a Cox hazard ratio derived from image feature metrics determined to be most relevant through machine learning techniques.

In some embodiments, a feature extraction module 205 is utilized to derive certain metrics from the received input images. In some embodiments, the derived metrics may be utilized by a classification module 206 such that cells, membranes, and/or nuclei may be identified and/or classified, e.g. as being a tumor cell or a non-tumor cell. In some embodiments, a scoring module 207 may be utilized to score an image (e.g. to provide an expression score), or a portion thereof (e.g. a region-of-interest), using the derived metrics and/or the classification results. In some embodiments, a multivariate Cox model module 208 may use a plurality of derived image feature metrics computed using the image feature extraction module 205 or may use prognostic features determined to be most relevant through machine learning using the prognostic feature derivation module 209. Each of these modules are described in more detail herein.

(1) Feature Extraction Module

The image data from each patient is first provided to a feature extraction module 205 such that image features may be ascertained (step 310). The skilled artisan will appreciate that the nucleus, cytoplasm and membrane of a cell have different characteristics and that differently stained tissue samples may reveal different biological features. Indeed, the skilled artisan will appreciate that certain cell surface receptors can have staining patterns localized to the membrane, or localized to the cytoplasm. Thus, a "membrane" staining pattern is analytically distinct from a "cytoplasmic" staining pattern. Likewise, a "cytoplasmic" staining pattern and a "nuclear" staining pattern are analytically distinct. Each of these distinct staining patterns may be used as features for identifying cells and/or nuclei. For example, stromal cells may be strongly stained by FAP, whereas tumor epithelial cells may be strongly stained by EpCAM, while cytokeratins may be stained by panCK. Thus, by utilizing different stains different cell types may be differentiated and distinguished during image analysis to provide a classification solution.

Methods of identifying, classifying, and/or scoring nuclei, cell membranes, and cell cytoplasm in images of biological samples having one or more stains are described in U.S. Pat. No. 7,760,927 ("the '927 Patent"), the disclosure of which is hereby incorporated by reference herein in its entirety for all purposes. For example, U.S. Pat. No. 7,760,927 describes an automated method for simultaneously identifying a plurality of pixels in an input image of a biological tissue stained with a biomarker, including considering a first color plane of a plurality of pixels in a foreground of the input image for simultaneous identification of cell cytoplasm and cell membrane pixels, wherein the input image has been processed to remove background portions of the input image and to remove counterstained components of the input image; determining a threshold level between cell cytoplasm and cell membrane pixels in the foreground of the digital image; and determining simultaneously with a selected pixel and its eight neighbors from the foreground if the selected pixel is cell cytoplasm pixel, a cell membrane pixel or a transitional pixel in the digital image using the determined threshold level.

In some embodiments, tumor nuclei are automatically identified by first identifying candidate nuclei and then automatically distinguishing between tumor nuclei and non-tumor nuclei. Numerous methods of identifying candidate nuclei in images of tissue are known in the art. For example, automatic candidate nucleus detection can be performed by applying a radial symmetry-based method, such as on the Hematoxylin image channel or a biomarker image channel after unmixing (see Parvin, Bahram, et al. "Iterative voting for inference of structural saliency and characterization of subcellular events." Image Processing, IEEE Transactions on 16.3 (2007): 615-623, the disclosure of which is incorporated by reference in its entirety herein for all purposes).

More specifically, in some embodiments the images received as input are processed such as to detect nucleus centers (seeds) and/or to segment the nuclei. For example, instructions may be provided to detect nucleus centers based on radial-symmetry voting using the techniques of Parvin (noted above). In some embodiments, nuclei are detected using radial symmetry to detect centers of nuclei and then the nuclei are classified based on the intensity of stains around the cell centers. In some embodiments, a radial symmetry based nuclei detection operation is used as described in commonly-assigned and co-pending patent application WO/2014/140085A1, the entirety of which is incorporated herein by reference for all purposes. For example, an image magnitude may be computed within an image and one or more votes at each pixel are accumulated by adding the summation of the magnitude within a selected region. Mean shift clustering may be used to find the local centers in the region, with the local centers representing actual nuclear locations. Nuclei detection based on radial symmetry voting is executed on color image intensity data and makes explicit use of the a priori domain knowledge that the nuclei are elliptical shaped blobs with varying sizes and eccentricities. To accomplish this, along with color intensities in the input image, image gradient information is also used in radial symmetry voting and combined with an adaptive segmentation process to precisely detect and localize the cell nuclei. A "gradient" as used herein is, for example, the intensity gradient of pixels calculated for a particular pixel by taking into consideration an intensity value gradient of a set of pixels surrounding said particular pixel. Each gradient may have a particular "orientation" relative to a coordinate system whose x- and y-axis are defined by two orthogonal edges of the digital image. For instance, nuclei seed detection involves defining a seed as a point which is assumed to lie inside a cell nucleus and serve as the starting point for localizing the cell nuclei. The first step is to detect seed points associated with each cell nuclei using a highly robust approach based on the radial symmetry to detect elliptical-shaped blobs, structures resembling cell nuclei. The radial symmetry approach operates on the gradient image using a kernel based voting procedure. A voting response matrix is created by processing each pixel that accumulates a vote through a voting kernel. The kernel is based on the gradient direction computed at that particular pixel and an expected range of minimum and maximum nucleus size and a voting kernel angle (typically in the range $[\pi/4, \pi/8]$). In the resulting voting space, local maxima locations that have a vote value higher than a predefined threshold value are saved out as seed points. Extraneous seeds may be discarded later during subsequent segmentation or classification processes. Other methods are discussed in US Patent Publication No. 2017/0140246, the disclosure of which is incorporated by reference herein for all purposes.

Nuclei may be identified using other techniques known to those of ordinary skill in the art. For example, an image magnitude may be computed from a particular image channel of one of the H&E or IHC images, and each pixel around a specified magnitude may be assigned a number of votes that is based on a summation of the magnitude within a region around the pixel. Alternatively, a mean shift clustering operation may be performed to find the local centers within a voting image, which represents the actual location of the nucleus. In other embodiments, nuclear segmentation may be used to segment the entire nucleus based on the now-known centers of the nuclei via morphological operations and local thresholding. In yet other embodiments, model based segmentation may be utilized to detect nuclei (i.e. learning the shape model of the nuclei from a training data set and using that as the prior knowledge to segment the nuclei in the testing image).

In some embodiments, the nuclei are then subsequently segmented using thresholds individually computed for each nucleus. For example, Otsu's method may be used for segmentation in a region around an identified nucleus since it is believed that the pixel intensity in the nuclear regions varies. As will be appreciated by those of ordinary skill in the art, Otsu's method is used to determine an optimal threshold by minimizing the intra-class variance and is known to those of skill in the art. More specifically, Otsu's method is used to automatically perform clustering-based image thresholding or, the reduction of a gray level image to a binary image. The algorithm assumes that the image contains two classes of pixels following a bi-modal histogram (foreground pixels and background pixels). It then calculates the optimum threshold separating the two classes such that their combined spread (intra-class variance) is minimal, or equivalent (because the sum of pairwise squared distances is constant), so that their inter-class variance is maximal.

In some embodiments, the systems and methods further comprise automatically analyzing spectral and/or shape features of the identified nuclei in an image for identifying nuclei of non-tumor cells. For example, blobs may be identified in the first digital image in a first step. A "blob" as used herein can be, for example, a region of a digital image in which some properties, e.g. the intensity or grey value, are constant or vary within a prescribed range of values. All pixels in a blob can be considered in some sense to be similar to each other. For example, blobs may be identified using differential methods which are based on derivatives of a function of position on the digital image, and methods based on local extrema. A nuclear blob is a blob whose pixels and/or whose outline shape indicate that the blob was probably generated by a nucleus stained with the first stain. For example, the radial symmetry of a blob could be evaluated to determine if the blob should be identified as a nuclear blob or as any other structure, e.g. a staining artifact. For example, in case a blob has a lengthy shape and is not radially symmetric, said blob may not be identified as a nuclear blob but rather as a staining artifact. Depending on the embodiment, a blob identified to be a "nuclear blob" may represent a set of pixels which are identified as candidate nuclei and which may be further analyzed for determining if said nuclear blob represents a nucleus. In some embodiments, any kind of nuclear blob is directly used as an "identified nucleus." In some embodiments, filtering operations are applied on the identified nuclei or nuclear blobs for identifying nuclei which do not belong to biomarker-positive tumor cells and for removing said identified non-tumor nuclei from the list of already identified nuclei or not adding said nuclei to the list of identified nuclei from the beginning. For example, additional spectral and/or shape features of the identified nuclear blob may be analyzed to determine if the nucleus or nuclear blob is a nucleus of a tumor cell or not. For example, the nucleus of a lymphocyte is larger than the nucleus of other tissue cell, e.g. of a lung cell. In case the tumor cells are derived from a lung tissue, nuclei of lymphocytes are identified by identifying all nuclear blobs of a minimum size or diameter which is significantly larger than the average size or diameter of a normal lung cell nucleus. The identified nuclear blobs relating to the nuclei of lymphocytes may be removed (i.e., "filtered out from") the set of already identified nuclei. By filtering out the nuclei of non-tumor cells, the accuracy of the method may be increased. Depending on the biomarker, also non-tumor cells may express the biomarker to a certain extent, and may therefore produce an intensity signal in the first digital image which does not stem from a tumor cell. By identifying and filtering out nuclei which do not belong to tumor cells from the totality of the already identified nuclei, the accuracy of identifying biomarker-positive tumor cells may be increased. These and other methods are described in US Patent Publication 2017/0103521, the disclosure of which is incorporated by reference herein in its entirety for all purposes. In some embodiments, once the seeds are detected, a locally adaptive thresholding method may be used, and blobs around the detected centers are created. In some embodiments, other methods may also be incorporated, such as marker based watershed algorithms can also be used to identify the nuclei blobs around the detected nuclei centers. These and other methods are described in co-pending application PCT/EP2016/051906, published as WO2016/120442, the disclosure of which is incorporated by reference herein in its entirety for all purposes.

Following detection of the nuclei, features (or metrics) are derived from within the input image. The derivation of metrics from nuclear features are well known in the art and any nuclear features known may be used in the context of the present disclosure. Non-limiting examples of metrics that may be computed include:

(A) Metrics Derived from Morphology Features

A "morphology feature" as used herein is, for example, a feature being indicative of the shape or dimensions of a nucleus. Without wishing to be bound by any particular theory, it is believed that morphological features provide some vital information about the size and shape of a cell or its nucleus. For example, a morphology feature may be computed by applying various image analysis algorithms on pixels contained in or surrounding a nuclear blob or seed. In some embodiments, the morphology features include area, minor, and major axis lengths, perimeter, radius, solidity, etc. At the cellular level, such features are used to classify a nucleus as belonging to a healthy or diseased cell. At the tissue level, the statistics of these features over the tissue are exploited in the classification of a tissue as diseased or not.

(B) Metrics Derived from Appearance Features

An "appearance feature" as used herein is, for example, a feature having been computed for a particular nucleus by comparing pixel intensity values of pixels contained in or surrounding a nuclear blob or seed used for identifying the nucleus, whereby the compared pixel intensities are derived from different image channels (e.g. a background channel, a channel for the staining of a biomarker, etc.). In some embodiments, the metrics derived from appearance features are computed from percentile values (e.g. the 10th, 50th, and 95th percentile values) of pixel intensities and of gradient magnitudes computed from different image channels. For example, at first, a number P of X-percentile values (X=10, 50, 95) of pixel values of each of a plurality IC of image channels (e.g. three channels: HTX, DAB, luminance) within a nuclear blob representing the nucleus of interest are identified. Computing appearance feature metrics may be advantageous since the derived metrics may describe the properties of the nuclear regions as well as describe the membrane region around the nuclei.

(C) Metrics Derived from Background Features

A "background feature" is, for example, a feature being indicative of the appearance and/or stain presence in cytoplasm and cell membrane features of the cell comprising the nucleus for which the background feature was extracted from the image. A background feature and a corresponding metrics can be computed for a nucleus and a corresponding cell depicted in a digital image e.g. by identifying a nuclear blob or seed representing the nucleus; analyzing a pixel area (e.g. a ribbon of 20 pixels—about 9 microns—thickness around the nuclear blob boundary) directly adjacent to the identified set of cells are computed in, therefore capturing appearance and stain presence in cytoplasm and membrane of the cell with this nucleus together with areas directly adjacent to the cell. These metrics are similar to the nuclear appearance features, but are computed in a ribbon of about 20 pixels (about 9 microns) thickness around each nucleus boundary, therefore capturing the appearance and stain presence in the cytoplasm and membrane of the cell having the identified nucleus together with areas directly adjacent to the cell. Without wishing to be bound by any particular theory, the ribbon size is selected because it is believed that it captures a sufficient amount of background tissue area around the nuclei that can be used to provide useful information for nuclei discrimination. These features are similar to those disclosed by "J. Kong, et al., "A comprehensive framework for classification of nuclei in digital microscopy imaging: An application to diffuse gliomas," in ISBI, 2011, pp.2128-2131" the disclosure of which is incorporated by reference in its entirety herein for all purposes. It is believed that these features may be used to determine whether the surrounding tissue is stroma or epithelium (such as in H&E stained tissue samples). Without wishing to be bound by any particular theory, it is believed that these background features also capture membrane staining patterns, which are useful when the tissue samples are stained with appropriate membrane staining agents.

(D) Metrics Derived from Color

In some embodiments, metrics derived from color include color ratios, R/(R+G+B). or color principal components. In other embodiments, metrics derived from color include local statistics of each of the colors (mean/median/variance/std dev) and/or color intensity correlations in a local image window.

(E) Metrics Derived from Intensity Features

The group of adjacent cells with certain specific property values is set up between the dark and the white shades of grey colored cells represented in a histopathological slide image. The correlation of the color feature defines an instance of the size class, thus this way the intensity of these colored cells determines the affected cell from its surrounding cluster of dark cells.

(F) Metris Derived from Texture Features

Examples of texture features and methods of their derivation are described in PCT Publication Nos. WO/2016/075095 and WO/2016/075096, the disclosures of which is incorporated by reference herein in their entireties for all purposes.

(G) Metrics Derived from Spatial Features

In some embodiments, spatial features include a local density of cells; average distance between two adjacent detected cells; and/or distance from a cell to a segmented region.

(H) Metrics Derived from Nuclear Features

The skilled artisan will also appreciate that metrics may also be derived from nuclear features. The computation of such nuclear features is described by Xing et al. "Robust Nucleus/Cell Detection and Segmentation in Digital Pathology and Microscopy Images: A Comprehensive Review," IEEE Rev Biomed Eng 9, 234-263, January 2016, the disclosure of which is hereby incorporated by reference herein in its entirety for all purposes.

Of course, other features, as known to those of ordinary skill in the art, may be considered and used as the basis for computation of features.

By way of another example, cells may be classified as lymphocytes, such as described in PCT Publication No. WO/2016/075096, the disclosure of which is incorporated by reference herein in its entirety for all purposes. In particular, PCT Publication No. WO/2016/075096 describes a computer-implemented method of classifying cells within an image of a tissue sample stained in an IHC assay for the presence of a PD-L1 biomarker comprising computing nuclear feature metrics from features of nuclei within the image of the tissue sample; computing contextual information metrics based on nuclei of interest with the image of the tissue sample; and classifying the cells within the image of the tissue sample using a combination of the nuclear feature metrics and contextual information metrics (as input of the classifier), wherein the cells are classified as at least one of positive immune cells, positive tumor cells, negative immune cells, and negative tumor cells, or other cells. In some embodiments, the method further comprises the step of creating a foreground segmentation mask to identify individual nuclei within the cells. The publication further describes that, in the context of PD-L1-stained tissue, regions with lymphocytes that do not express the PD-L1 biomarker ("negative lymphocytes") are characterized by small blue blobs; regions with lymphocytes that do express the PD-L1 biomarker ("positive lymphocytes") are characterized by small blue blobs and brown blobs; tumor regions with cells predominantly expressing the PD-L1 biomarker ("positive tumor cells") are characterized by large blue blobs and brown rings; and tumor regions where cells do not express the PD-L1 biomarker ("negative tumor cells") are characterized by large blue blobs only.

(2) Classification Module

After image feature metrics are derived using the feature extraction module 205, the image feature metrics may be used alone or in conjunction with training data (e.g. during training, example cells are presented together with a ground truth identification provided by an expert observer according to procedures known to those of ordinary skill in the art) to classify nuclei or cells (using the classification module 206). In some embodiments, the system can include a classifier that was trained based at least in part on a set of training or reference slides for each biomarker. The skilled artisan will appreciate that different sets of slides can be used to train a classifier for each biomarker. Accordingly, for a single biomarker, a single classifier is obtained after training. The skilled artisan will also appreciate that since there is variability between the image data obtained from different biomarkers, a different classifier can be trained for each different biomarker so as to ensure better performance on unseen test data, where the biomarker type of the test data will be known. The trained classifier can be selected based at least in part on how best to handle training data variability, for example, in tissue type, staining protocol, and other features of interest, for slide interpretation.

In some embodiments, the classification module 206 comprises a Support Vector Machine ("SVM"). In general, a SVM is a classification technique, which is based on statistical learning theory where a nonlinear input data set is converted into a high dimensional linear feature space via kernels for the non-linear case. Without wishing to be bound by any particular theory, it is believed that support vector machines project a set of training data, E, that represents two different classes into a high-dimensional space by means of a kernel function, K. In this transformed data space, non-linear data are transformed so that a flat line can be generated (a discriminating hyperplane) to separate the classes so as to maximize the class separation. Testing data are then projected into the high-dimensional space via K, and the test data are classified on the basis of where they fall with respect to the hyperplane. The kernel function K defines the method in which data are projected into the high-dimensional space.

In other embodiments, classification is performed using an AdaBoost algorithm. The AdaBoost is an adaptive algorithm which combines a number of weak classifiers to generate a strong classifier. Image pixels identified by a pathologist during the training stage (e.g. those having a particular stain or belonging to a particular tissue type) are used to generate probability density functions for each of the individual texture features $\Phi j$, for $j \in \{1, \ldots, K\}$ which are considered as weak classifiers. Bayes Theorem is then used to generate likelihood scenes $Lj=(Cj, 1\ j \in \{1, \ldots, K\})$ for each $\Phi j$ which constitute the weak learners. These are combined by the AdaBoost algorithm into a strong classifier $\Pi j = \Sigma T i = 1 \alpha j i l j i$ where for every pixel $cj \in Cj$, $\Pi j$ (cj) is the combined likelihood that pixel cj belongs to class $\omega T$, where $\alpha ji$ is the weight determined during training for feature $\Phi i$, and T is the number of iterations.

(3) Scoring Module

Following the derivation of image feature metrics and/or classification of the cells/nuclei, a scoring module 207 is utilized to provide an expression score based on the derived image feature metrics. Non-limiting examples of diagnostic metrics include, without limitation, percent positivity, an Allred score, an immunohistochemistry combination score, or an H-score. The skilled artisan will appreciate that any of these examples of expression scores may be used as the derived diagnostic feature (step 320). In some embodiments, expression scores from the scoring module are utilized as diagnostic metrics.

For example, the feature extraction module 205 may comprise a series of image analysis algorithms and be used to determine a presence of one or more of a nucleus, a cell wall, a tumor cell, or other structures within the identified cell clusters, as described herein. In some embodiments, derived stain intensity values and counts of specific nuclei for each field of view may be used to determine various marker expression scores, such as percent positivity or an H-Score. Methods for scoring are described in further detail in commonly-assigned and co-pending applications WO/2014/102130A1 "Image analysis for breast cancer prognosis" filed Dec. 19, 2013, and WO/2014/140085A1 "Tissue object-based machine learning system for automated scoring of digital whole slides", filed Mar. 12, 2104, the contents of each are hereby incorporated by reference in their entirety herein for all purposes.

By way of example, automated image analysis algorithms in the scoring module 207 may be used to interpret each one of the IHC slides in the series to detect tumor nuclei that are positively and negatively stained for a particular biomarker, such as Ki67, ER, PR, HER2, etc. Based on the detected positive and negative tumor nuclei, various slide level scores such as marker percent positivity, H-scores, etc. may be computed using one or more methods.

In some embodiments, the expression score is an H-score. In some embodiments, the 'H' score is used to assess the percentage of tumor cells with cell membrane staining graded as 'weak,' 'moderate' or 'strong.' The grades are summated to give an overall maximum score of 300 and a cut-off point of 100 to distinguish between a 'positive' and 'negative.' For example, a membrane staining intensity (0, 1+, 2+, or 3+) is determined for each cell in a fixed field of view (or here, each cell in a tumor or cell cluster). The H-score may simply be based on a predominant staining intensity, or more complexly, can include the sum of individual H-scores for each intensity level seen. By one method, the percentage of cells at each staining intensity level is calculated, and finally, an H-score is assigned using the following formula: [1×(% cells 1+)+2×(% cells 2+)+3×(% cells 3+)]. The final score, ranging from 0 to 300, gives more relative weight to higher-intensity membrane staining in a given tumor sample. The sample can then be considered positive or negative on the basis of a specific discriminatory threshold. Additional methods of calculating an H-score are described in United States Patent Publication 2015/0347702, the disclosure of which is hereby incorporated by reference herein in its entirety for all purposes.

In some embodiments, the expression score is an Allred score. The Allred score is a scoring system which looks at the percentage of cells that test positive for hormone receptors, along with how well the receptors show up after staining (this is called "intensity"). This information is then combined to score the sample on a scale from 0 to 8. The higher the score, the more receptors are found and the easier they are to see in the sample.

In other embodiments, the expression score is percent positivity. Again, in the context of scoring a breast cancer sample stained for the PR and Ki-67 biomarkers, for the PR and Ki-67 slides, the percent positivity is calculated (e.g., the total number of nuclei of cells (e.g., malignant cells) that are stained positive in each field of view in the digital image of a slide are summed and divided by the total number of positively and negatively stained nuclei from each of the fields of view of a digital image) in a single slide as follows: Percent positivity=number of positively stained cells/(number of positively stained cells+number of negatively stained cells).

In other embodiments, the expression score is an immunohistochemistry combination score, which is a prognostic score based on a number of IHC markers, wherein the number of markers is greater than one. IHC4 is one such score based on four measured IHC markers, namely ER, HER2, Ki-67, and PR in a breast cancer sample (for example see Cuzick et al., J. Clin. Oncol. 29:4273-8, 2011, and Barton et al., Br. J. Cancer 1-6, Apr. 24, 2012, both herein incorporated by reference for all purposes). In one example, and in the context of detecting expression scores for breast cancer, an IHC4 score is calculated using, for example, the following formula:

$$IHC4=94.7\times\{-0.100ER10-0.079PR10+0.586HER2+0.240\ln(1+10\times Ki67)\}.$$

(4) Multivariate Cox Model Module

In some embodiments, if multiple diagnostic features are selected (such as by a pathologist), a multivariate Cox model may be constructed to yield a diagnostic feature metric (step 320) that comprises a weighed combination of multiple metrics (e.g. multiple image feature metrics and/or expression scores). In some embodiments, the multiple diagnostic feature metrics are derived using the feature extraction module 205, the classification module 206, and/or scoring module 207. For example, the multiple metrics may be image feature metrics or expression scores. Again, by way of example, the Cox model module may weight and combine an H-score and a biomarker percent positivity. Alternatively, multiple metrics may be combined where the multiple metrics are determined through a machine learning method using the prognostic feature derivation module 209.

Cox's proportional hazards model is analogous to a multiple regression model and enables the difference between, for example, survival times of particular groups of patients to be tested while allowing for other factors. In general, it is a survival analysis regression model, which describes the relation between the event incidence, as expressed by the hazard function and a set of covariates. In this model, the response (dependent) variable is the 'hazard'. The hazard is the instantaneous event probability at a given time, or the probability that an individual under observation experiences the event in a period centered around that point in time. In the context of survival analysis, the hazard is the probability of dying given that patients have survived up to a given point in time, or the risk for death at that moment.

Mathematically, the Cox model is written as:

$$h(x,t)=h_0(t)\times\exp\{b_1x_1+b_2x_2+\ldots+b_px_p\}$$

where the hazard function h(x,t) is dependent on (or determined by) a set of p covariates $(x_1, x_2, \ldots, x_p)$, whose impact is measured by the size of the respective coefficients $(b_1, b_2, \ldots, b_p)$. The term $h_0$ is called the baseline hazard, and is the value of the hazard if all the $x_i$ are equal to zero (the quantity exp(0) equals 1). The 't' in h(t) reminds us that the hazard may (and probably will) vary over time. An appealing feature of the Cox model is that the baseline hazard function is estimated non-parametrically, and so unlike most other statistical models, the survival times are not assumed to follow a particular statistical distribution. As applied here, the p covariates are the various diagnostic features values under consideration.

The Cox model is essentially a multiple linear regression of the logarithm of the hazard on the variables $x_i$, with the baseline hazard being an 'intercept' term that varies with time. The covariates then act multiplicatively on the hazard at any point in time, and this provides us with the key assumption of the PH model: the hazard of the event in any group is a constant multiple of the hazard in any other. This assumption implies that the hazard curves for the groups should be proportional and cannot cross. Proportionality implies that the quantities exp($b_i$) are called hazard ratios. A value of $b_i$ greater than zero, or equivalently a hazard ratio greater than one, indicates that as the value of the i-th covariate increases, the event hazard increases and thus the length of survival decreases. Put another way, a hazard ratio above 1 indicates a covariate that is positively associated with the event probability, and thus negatively associated with the length of survival.

In some embodiments, for each patient sample of the test cohort, data is obtained regarding the outcome being tracked (time to death, time to recurrence, or time to progression) and the feature metric for each biomarker being analyzed. Candidate Cox proportional models are generated by entering the diagnostic feature data and survival data for each individual of the cohort into a computerized statistical analysis software suite (such as The R Project for Statistical Computing (available at https://www.r-project.org/), SAS, MATLAB, among others).

Following construction of the Cox model, the hazard function (h(x,t)) may be used as a diagnostic feature (step 320).

(5) Prognostic Feature Derivation Module

In some embodiments, a machine learning algorithm may be utilized to determine a set of image feature metrics that are most relevant in predicting a patient outcome. Said another way, rather than use pre-specified image expression scores or image feature metrics (or any combination thereof, such as combined in a multivariate Cox model), a machine learning technique may be used to discover features which may be more accurate in predicting a response, i.e. a data-driven diagnostic feature discovery method. In some embodiments, prognostic feature derivation module 209 may be utilized to validate the predictive value of novel image feature metrics.

In some embodiments, the input data (image data and patient data) may be derived from a placebo arm of a clinical trial (either Phase II and/or Phase III), and a classifier may be used to determine those image and clinical features which are believed to be important in a binary categorization of patients. In other embodiments, the input data (image data and patient data) may be derived from a drug study arm of a clinical trial (either Phase II and/or Phase III), and a classifier may be used to determine those image and clinical features which are believed to be important in a binary categorization of patients. For example, input images from a patient population may comprise 100 image feature metrics after image analysis. A machine learning algorithm may be utilized to determine which of those 100 image feature metrics best predict the patient population outcome and, by way of example, this may be 10 top image feature metrics from the 100 total image feature metrics. Again, by way of example, these 10 top image feature metrics may be combined using a multivariate Cox hazard model to provide a diagnostic feature that may be utilized for further downstream processing.

Figure 5:
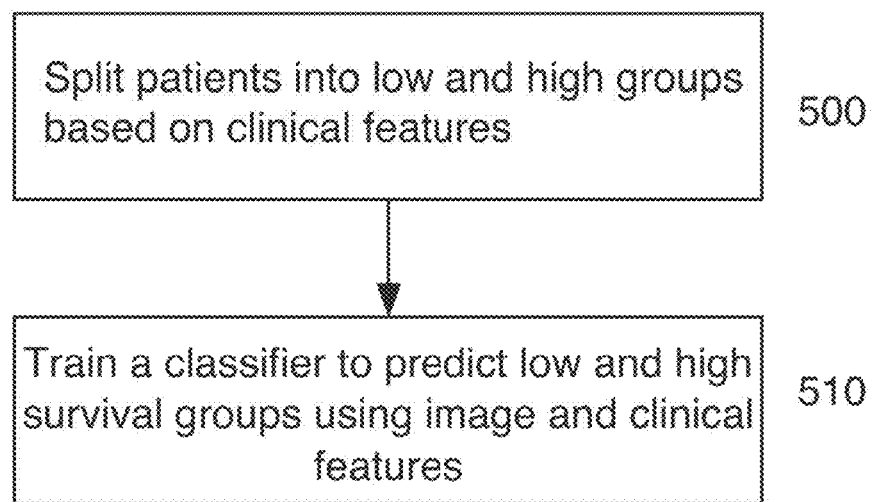
FIG. 5 sets forth a flowchart illustrating the steps of applying machine learning to retrospectively analyze clinical trial data.

In some embodiments, a diagnostic feature metric (step 320) is determined using a machine-based learning technique. In some embodiments, a binary classification problem is created to train the classifier. With reference to FIG. 5, patients are split into low and high survival groups (step 500). The determination of which patients in a cohort fall into a particular group may be based, for example, on a threshold overall survival time, such as a threshold of a predetermined number of months, e.g. 7-months. More specifically, a particular cohort of patients may be classified into (i) those that survived less than a median survival time (e.g. those that survived less than a predetermined median OS); and (ii) those that survived more than a median survival time (e.g. those that survived more than a predetermined median OS). Then a classifier is built (step 510) using the image feature metrics derived at step 310.

Once trained, the classifier may then be utilized to determine those image features in test images that best correspond to certain patient outcome data. As noted above, such prognostic features differ from pre-specified diagnostic features (such as H-score) in that that image and clinical features are derived from image data that most accurately stratifies patient populations or cohorts. The prognostic feature set is then supplied to the multivariate Cox model module 208 to provide a diagnostic feature metric (step 320) for use in downstream processing, i.e. a multivariate Cox model is built using the multiple prognostic features from the classifier.

Cutoff Determination Module

In medical research and, in particular, cancer research, when a survival analysis is conducted, it is a common practice to dichotomize a continuous covariate. In some embodiments, a derived diagnostic feature (from step 320) and patient outcome data (from database 212) may be used as input in a bio-statistical analysis to find an optimal cutoff for a scoring diagnostic. In view of this, the diagnostic feature from step 320 is then provided, along with patient outcome data (from database 212) to the cutoff determination module 210 such that a cutoff point or cut point (used interchangeably herein) may be determined (step 330).

In some embodiments, a log rank statistic minimization method is utilized to determine a cutoff value. Compared to data dependent methods, a long rank statistic based method finds a statistically optimal solution. The log rank statistic method is a commonly used procedure for comparing two survival distributions (e.g. a placebo cohort and a treatment cohort). It is a nonparametric test and it is believed that the method is appropriate to use when the data are right skewed and censored.

Let R be the risk factor of interest measured as a continuous variable and T be the outcome variable. In case of survival analysis, the outcome of interest T, is oftentimes time to death but it can also be time to some other event of interest. In some embodiments, the population is divided into two groups based on the cut point: subjects with the value of the risk factor less than or equal to the value of the cut point and subjects with the value of the risk factor greater than the cut point. Let $t(1)<t(2)< \ldots <t(k)$ be the ordered observed event times of the outcome variable T. Let C be the set of K distinct values of the continuous covariate R. Then, based on one hypothetical cut point from C, let d(i) be the number of events at time t(1), r(i) be the number of subjects at risk prior to time t(i) and d(i)+ and r(i)+ be the number of events at time t(i) in group R>C and number of subjects at risk just prior to t(i) in the group R>C. Similarly, d(i)− and r(i)− be the number of events at time t(i) in group R less than or equal to C and number of subjects at risk just prior to t(i) in the group R than or equal to C. Thus, the log rank statistic for some fixed C is given by:

$$\text{Log Rank Statistic} = L_k(t) = \sum_{i=1}^{k} \left( d_i^+ - d_i \frac{r_i^+}{r_i} \right)$$

The optimal cut point is that value of C, Ck that maximizes the absolute value of Lk (t). Ck therefore gives the value of the continuous covariate that gives the maximum difference between the subjects in the two groups defined by the cut point. The log rank statistic and other methods of determining cut points are described by L. Zhang and Y. Shu, "Advances in Visual Computing," 12th International Symposium, ISVC 2016, Dec. 12-14, 2016, Proceedings, Part 1, pp.57-63, the disclosure of which is hereby incorporated by reference herein in its entirety for all purposes. The optimal cut point will be the threshold on the diagnostic to identify a patient as positive or negative for the test.

Once the optimal cutoff point is determined (step 330), patients may be stratified into diagnostic positive and diagnostic negative groups (step 340). This automatic diagnostic cut point and the resultant stratification can, in some embodiments, be compared against a manually selected diagnostic cut point and stratification (step 350). In some embodiments, the comparison may assist in determining whether the correct companion diagnostic was used, or if the threshold set in a clinical trial was too high or too low, i.e. the impact of the manually selected diagnostic cut point may be determined (step 360).

(1) Drug Response Curve Generation Module

In some embodiments, drug response curves are generated (step 370) based on the stratified patient groups (from step 350). In some embodiments, the generated drug response curves may be used to determine if clinical efficacy exists in a Phase II or Phase III trial, the drug response curves used to compare control and drug study cohorts in either trial. In some embodiments, drug response curves are generated for both the placebo and the drug study cohorts.

In analyzing survival data, two functions that are dependent on time are of particular interest: the survival function and the hazard function. The survival function S(t) is defined as the probability of surviving at least to time t. The hazard function h(t) is the conditional probability of dying at time t having survived to that time.

The graph of S(t) against t is called the survival curve. The Kaplan-Meier method can be used to estimate this curve from the observed survival times without the assumption of an underlying probability distribution. The method is based on the basic idea that the probability of surviving k or more periods from entering the study is a product of the k observed survival rates for each period (i.e. the cumulative proportion surviving), given by the following:

$$S(k)=p_1 \times p_2 \times p_3 \times \ldots \times p_k$$

Here, $p_1$ is the proportion surviving the first period, $p_2$ is the proportion surviving beyond the second period conditional on having survived up to the second period, and so on. The proportion surviving period i having survived up to period i is given by: $p_i=(r_i-d_i)/r_i$ where $r_i$ is the number alive at the beginning of the period and $d_i$ the number of deaths within the period.

As such, a Kaplan-Meier curve is a statistical picture of the percentage of patients surviving over a period of time; it cannot be summed up with a single number such as median survival or a landmark measure (i.e. a measure of the number of people alive at a predetermined time). The slope of the curve is the overall rate of death or risk of death; this is called the hazard ratio or the hazard rate. For example, if a study has two arms (e.g. a placebo group and a group administered a drug), then two survival curves can be constructed, each with its own hazard rate. The hazard ratio ("HR") is the ratio of the hazard for the study drug group divided by the hazard for the placebo control group. If HR=1, the hazard or risk of death in the two groups is equal. If HR>1, the risk of death is increased in the study group compared with the control group, while HR<1 means the risk of death is decreased in the study group compared with the control group.

In some embodiments, the larger the separation of the curves the greater difference between the treatment groups in the endpoint being analyzed. If the treatment arms represented in the Kaplan-Meier curve follow a similar path, it suggests that there is only a small amount of difference between the arms of the study in the endpoint being measured. If the arms were to meet, that would mean at that particular time point there was no difference between the two arms of the study in the endpoint being measured.

Figure 6:
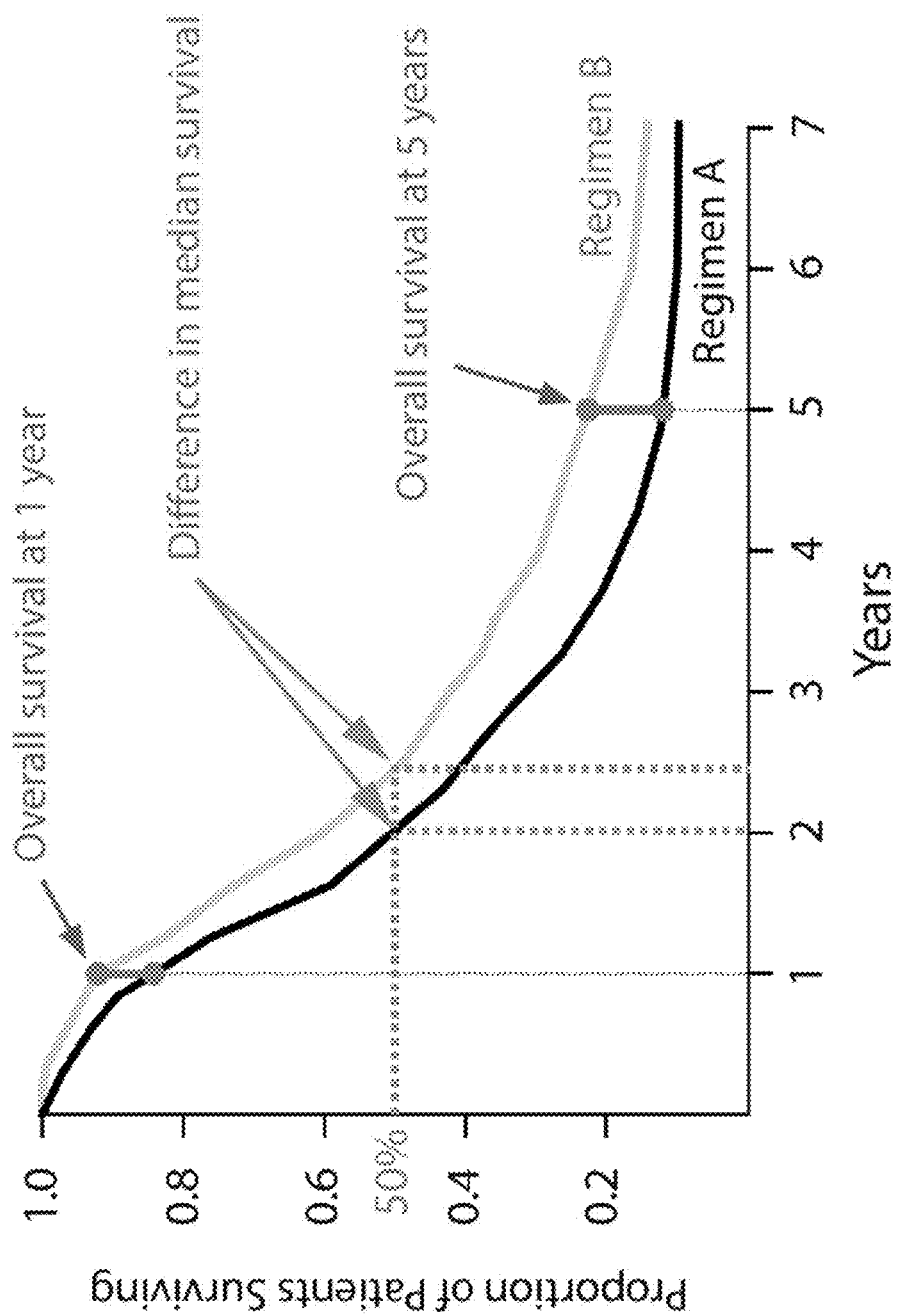
FIG. 6 provides an example of a drug-response curve.

FIG. 6 provides an illustrative example of a Kaplan-Meier curve to show the difference between the median and landmark overall survival measurements of two regimens, namely Regimen A and Regimen B (which could be a placebo group vs. a drug study group). In this particular example, the difference in median survival times appears to be relatively small, as does the difference in overall survival at one-year (93% vs 85%), whereas at five years the overall survival difference is 23% vs 12%. Because of the shape of the curves, however, there also may be a large difference in overall survival as measured by the hazard ratio.

Cohort Signature Module

As a byproduct of the whole tumor image analysis, a large quantity of image feature metrics are computed for each patient tissue slide. If genomic analysis of the patient's tissue sample is also performed, similarly a set of molecular and genomic variants are output for each patient (tissue analysis data). A feature vector may be generated by combining the image feature metrics and the genomic features/tissue analysis from each patient along with certain clinical attributes. In some embodiments, from the generated feature vectors of all of the patients in a given cohort, a feature matrix may be constructed. In some embodiments, a statistical analysis of the feature matrix (e.g. principal component analysis, hierarchical clustering of features followed up with feature selection) will yield a condensed feature matrix for the cohort called a "cohort signature," i.e. a matrix that characterizes the tissue feature variation along with feature correlations. In some embodiments, the statistical analysis allows one to determine whether two given cohorts are similar or different. Specifically, the statistical analysis can facilitate a determine of how similar or how different two datasets are, e.g. how similar or how different Phase II and Phase III cohorts are.

Figure 7:
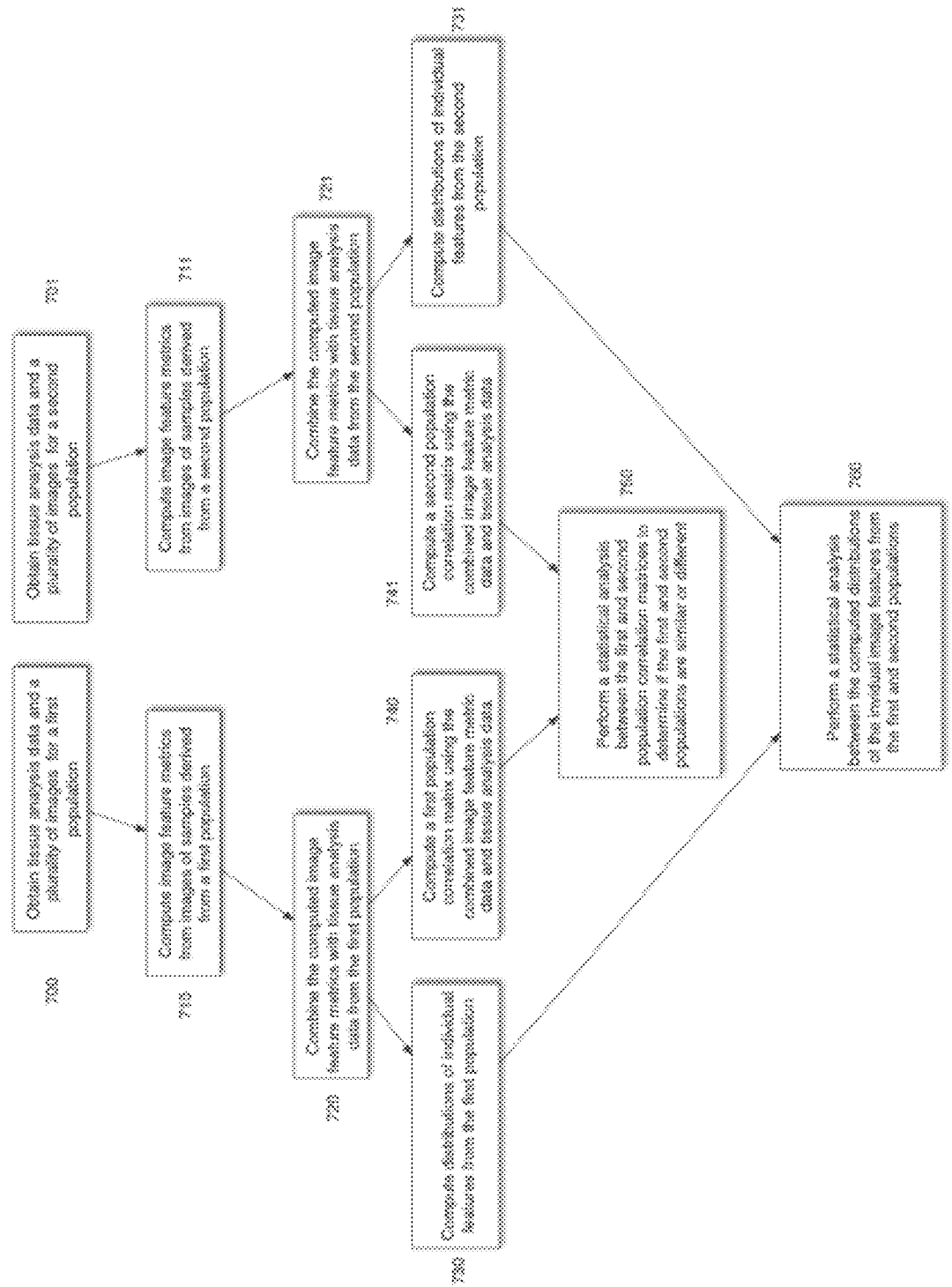
FIG. 7 sets forth a flow chart illustrating the steps of deriving cohort signatures and comparing how similar or how different patient populations are to each other.

With reference to FIG. 7, data is received or acquired from each of two different patient populations. In some embodiments, image data corresponding to biological samples from two different patient populations is received as input (steps 700 and 701). In some embodiments, the biological samples are stained with a primary stain and a counterstain (i.e. an H&E image) or stained for the presence of a particular biomarker (i.e. and IHC image). In addition to the image data, other tissue analysis data is also received for each patient in the patient populations. In some embodiments, the tissue analysis data is molecular or genomic data (such as genomic data stored in database 212).

Next, image feature metrics are computed (steps 710 and 711) for each of the images received as input and for each patient population. In some embodiments, the image feature metrics are computed using feature extraction module 205, the classification module 206, and/or the scoring module 207 and as described herein.

The computed image feature metrics are then combined with the tissue analysis data (steps 720 and 721) for each patient to provide a set of tissue features for each patient (e.g. a feature vector) in the patient populations. The tissue feature data together with clinical attributes for all patients, may then be utilized to generate a correlation matrix for each patient population. (steps 740 and 741). In some embodiments, the clinical attributes are age, weight, sex, ethnicity, etc. The correlation matrices for each of the two patient populations may then be compared using statistical methods to determine how similar or how different the patient populations are from each other (step 750).

In addition, distributions of individual tissue features may be computed for each of the patient populations (steps 730 and 731). The computed distributions may then be compared using statistical methods to again determine how similar or different the patient populations are to each other.

In some embodiments, the first patient population is a Phase II patient cohort, while the second patient population is a Phase III patient cohort. In some embodiments, the first patient population is a Phase II placebo cohort, while the second patient population is a Phase III placebo cohort. In some embodiments, the first patient population is a Phase II test arm cohort, while the second patient population is a Phase III placebo cohort. In some embodiments, the first patient population is a Phase II test arm cohort, while the second patient population is a Phase III test arm cohort. In some embodiments, the first patient population is a Phase II placebo cohort, while the second patient population is a Phase II test arm cohort. In some embodiments, the first patient population is data collected pre-treatment; while the second patient population is data collected from the same patients post-treatment.

Other Components for Practicing Embodiments of the Present Disclosure

Other components (e.g. systems or modules) are described below which may be used in conjugation with the systems and methods of the present disclosure.

(1) Unmixing Module

In some embodiments, the images received as input may be multiplex images, i.e. the image received is of a biological sample stained with more than one stain. In these embodiments, and prior to further processing, the multiple image is first unmixed into its constituent channels, where each unmixed channel corresponds to a particular stain or signal. In some embodiments, the unmixed images (often referred to as "channel images" or "image channel images") and may be used as the input for each module described herein. For example, inter-marker heterogeneity may be determined with a first H&E image, a second multiplex image stained for a plurality of cluster of differentiation markers (CD3, CD8, etc.), and a plurality of simplex images each stained for a particular biomarker (e.g. ER, PR, Ki67, etc.). In this example, the multiplex image is first unmixed into its constituent channel images, and those channel images may be used along with the H&E image and the plurality of simplex images to determined inter-marker heterogeneity.

In some embodiments, in a sample comprising one or more stains and hematoxylin, individual images may be produced for each channel of the one or more stains and hematoxylin. Without wishing to be bound by any particular theory, it is believed that these channels highlight different tissue structures in the tissue image, thus, they may be referred to as structural image channels. In some embodiments, unmixing provides at least a hematoxylin image channel image. In some embodiments, an acquired image is unmixed into a separate channel representing the local amounts of hematoxylin and highlighting nuclei regions within the image. The skilled artisan will appreciate that features extracted from these channels are useful in describing the different biological structures present within any image of a tissue.

The multi-spectral image provided by the imaging acquisition module 202 is a weighted mixture of the underlying spectral signals associated the individual biomarkers and noise components. At any particular pixel, the mixing weights are proportional to the biomarker expressions of the underlying co-localized biomarkers at the particular location in the tissue and the background noise at that location. Thus, the mixing weights vary from pixel to pixel. The spectral unmixing methods disclosed herein decompose the multichannel pixel value vector at each and every pixel into a collection of constituent biomarker end members or components and estimate the proportions of the individual constituent stains for each of the biomarkers.

Unmixing is the procedure by which the measured spectrum of a mixed pixel is decomposed into a collection of constituent spectra, or endmembers, and a set of corresponding fractions, or abundances, that indicate the proportion of each endmember present in the pixel. Specifically, the unmixing process can extract stain-specific channels to determine local concentrations of individual stains using reference spectra that are well known for standard types of tissue and stain combinations. The unmixing may use reference spectra retrieved from a control image or estimated from the image under observation. Unmixing the component signals of each input pixel enables retrieval and analysis of stain-specific channels, such as a hematoxylin channel and an eosin channel in H&E images, or a diaminobenzidine (DAB) channel and a counterstain (e.g., hematoxylin) channel in IHC images. The terms "unmixing" and "color deconvolution" (or "deconvolution") or the like (e.g. "deconvolving," "unmixed") are used interchangeably in the art.

In some embodiments, the multiplex images are unmixed with the feature extraction module 205 using liner unmixing. Linear unmixing is described, for example, in 'Zimmermann "Spectral Imaging and Linear Unmixing in Light Microscopy" Adv Biochem Engin/Biotechnol (2005) 95:245-265' and in in C. L. Lawson and R. J. Hanson, "Solving least squares Problems", Prentice Hall, 1974, Chapter 23, p. 161,' the disclosures of which are incorporated herein by reference in their entirety for all purposes. In linear stain unmixing, the measured spectrum ($S(\lambda)$) at any pixel is considered a linear mixture of stain spectral components and equals the sum of the proportions or weights (A) of each individual stain's color reference ($R(\lambda)$) that is being expressed at the pixel $$S(\lambda) = A_1 \times R_1(\lambda) + A_2 \times R_2(\lambda) + A_3 \times R_3(\lambda) \ldots A_i \times R_1(\lambda)$$

which can be more generally expressed as in matrix form as $$S(\lambda) = \Sigma A_i \times R_i(\lambda) \text{ or } S = R \times A$$

If there are M channels images acquired and N individual stains, the columns of the M×N matrix R are the optimal color system as derived herein, the N×1 vector A is the unknown of the proportions of individual stains and the M×1 vector S is the measured multichannel spectral vector at a pixel. In these equations, the signal in each pixel (S) is measured during acquisition of the multiplex image and the reference spectra, i.e. the optimal color system, is derived as described herein. The contributions of various stains ($A_i$) can be determined by calculating their contribution to each point in the measured spectrum. In some embodiments, the solution is obtained using an inverse least squares fitting approach that minimizes the square difference between the measured and calculated spectra by solving the following set of equations, $$[\partial \Sigma_j \{S(\lambda_j) - \Sigma_i A_i \times R_i(\lambda_j)\}2]/\partial A_i = 0$$

In this equation, j represents the number of detection channels and i equals the number of stains. The linear equation solution often involves allowing a constrained unmixing to force the weights (A) to sum to unity.

In other embodiments, unmixing is accomplished using the methods described in WO2014/195193, entitled "Image Adaptive Physiologically Plausible Color Separation," filed on May 28, 2014, the disclosure of which is hereby incorporated by reference in its entirety herein for all purposes. In general, WO2014/195193 describes a method of unmixing by separating component signals of the input image using iteratively optimized reference vectors. In some embodiments, image data from an assay is correlated with expected or ideal results specific to the characteristics of the assay to determine a quality metric. In the case of low quality images or poor correlations against ideal results, one or more reference column vectors in matrix R are adjusted, and the unmixing is repeated iteratively using adjusted reference vectors, until the correlation shows a good quality image that matches physiological and anatomical requirements. The anatomical, physiological, and assay information may be used to define rules that are applied to the measured image data to determine the quality metric. This information includes how the tissue was stained, what structures within the tissue were intended or not intended to be stained, and relationships between structures, stains, and markers specific to the assay being processed. An iterative process results in stain-specific vectors that can generate images that accurately identify structures of interest and biologically relevant information, are free from any noisy or unwanted spectra, and therefore fit for analysis. The reference vectors are adjusted to within a search space. The search space defines a range of values that a reference vector can take to represent a stain. The search space may be determined by scanning a variety of representative training assays including known or commonly occurring problems, and determining high-quality sets of reference vectors for the training assays.

In other embodiments, unmixing is accomplished using the methods described in WO2015/124772, entitled "Group Sparsity Model for Image Unmixing," filed on Feb. 23, 2015, the disclosure of which is hereby incorporated by reference in its entirety herein for all purposes. In general, WO2015/124772 describes unmixing using a group sparsity framework, in which fractions of stain contributions from a plurality of colocation markers are modeled within a "same group" and fractions of stain contributions from a plurality of non-colocation markers are modeled in different groups, providing co-localization information of the plurality of colocation markers to the modeled group sparsity framework, solving the modeled framework using a group lasso to yield a least squares solution within each group, wherein the least squares solution corresponds to the unmixing of the colocation markers, and yielding a sparse solution among the groups that corresponds to the unmixing of the non-colocation markers. Moreover, WO2015124772 describes a method of unmixing by inputting image data obtained from the biological tissue sample, reading reference data from an electronic memory, the reference data being descriptive of the stain color of each one of the multiple stains, reading colocation data from electronic memory, the colocation data being descriptive of groups of the stains, each group comprising stains that can be collocated in the biological tissue sample, and each group forming a group for the group lasso criterion, at least one of the groups having a size of two or above, and calculating a solution of the group lasso criterion for obtaining the unmixed image using the reference data as a reference matrix. In some embodiments, the method for unmixing an image may comprise generating a group sparsity model wherein a fraction of a stain contribution from colocalized markers is assigned within a single group and a fraction of a stain contribution from non-colocalized markers is assigned within separate groups, and solving the group sparsity model using an unmixing algorithm to yield a least squares solution within each group.

Additional Embodiments

In some embodiments, to retrospectively evaluate the impact of the treatment along with other patient attributes (tissue, clinical and pathological) a data-driven machine learning approach is disclosed. The tissue attributes can be a combination of image, genomic and molecular features measured and/or derived from the patient tissue. The machine learning approach can be a regression model or classifier model. To build the regression model, the complete survival data is used. In the regression model, the model predicts the probability of favorable response from a given patient data. To build a classifier model, based on a user specified threshold value on the patient outcome data (overall survival, PFS, RFS, complete response), the patient pool is categorized into two patients pools of favorable and unfavorable response groups. In classifier model, the classifier predicts whether a particular patient falls in the favorable or unfavorable response group. And with all the patient attributes as feature data, a regression or binary classifier model. The learnt model, in addition to learning to predict the drug response, can discover and output a set of important features, predictive attributes, that explain the observed patient responses in the study. Thus, it can inform whether if the drug or the treatment is a predictive attribute; and/or if any other patients attributes explain the patient response and a combination of multiple and interacting features better inform about the cohort result data. And this new information, can guide in recognizing a subset of the Phase III population for whom the treatment or drug results in a favorable response; or else design a different prospective study to account for the newly discovered set of features.

Other System Components

The digital pathology system 200 of the present disclosure may be tied to a specimen processing apparatus that can perform one or more preparation processes on the tissue specimen. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

The processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the paraffin is removed, any number of substances can be successively applied to the specimen. The substances can be for pretreatment (e.g., to reverse protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. In some embodiments, the imaging apparatus is a brightfield imager slide scanner. One brightfield imager is the iScan Coreo brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entirety for all purposes.

The imaging system or apparatus may be a multispectral imaging (MSI) system or a fluorescent microscopy system. The imaging system used here is an MSI. MSI, generally, equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

An MSI system may include an optical imaging system, a portion of which contains a spectrally-selective system that is tunable to define a pre-determined number N of discrete optical bands. The optical system may be adapted to image a tissue sample, illuminated in transmission with a broadband light source onto an optical detector. The optical imaging system, which in one embodiment may include a magnifying system such as, for example, a microscope, has a single optical axis generally spatially aligned with a single optical output of the optical system. The system forms a sequence of images of the tissue as the spectrally selective system is being adjusted or tuned (for example with a computer processor) such as to assure that images are acquired in different discrete spectral bands. The apparatus may additionally contain a display in which appears at least one visually perceivable image of the tissue from the sequence of acquired images. The spectrally-selective system may include an optically-dispersive element such as a diffractive grating, a collection of optical filters such as thin-film interference filters or any other system adapted to select, in response to either a user input or a command of the pre-programmed processor, a particular pass-band from the spectrum of light transmitted from the light source through the sample towards the detector.

An alternative implementation, a spectrally selective system defines several optical outputs corresponding to N discrete spectral bands. This type of system intakes the transmitted light output from the optical system and spatially redirects at least a portion of this light output along N spatially different optical paths in such a way as to image the sample in an identified spectral band onto a detector system along an optical path corresponding to this identified spectral band.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

All of the U.S. patents, U.S. patent application publications, U.S. patent applications, foreign patents, foreign patent applications and non-patent publications referred to in this specification and/or listed in the Application Data Sheet are incorporated herein by reference, in their entirety for all purposes. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method comprising:
accessing a plurality of images derived from biological samples of subjects in a cohort population, the biological samples having at least one stain;
computing, based on the plurality of images, one or more image features;
deriving a diagnostic feature metric based on the computed image features; and
determining a cut point value by applying a statistical minimization method using the derived diagnostic feature metric and subject outcome data from the cohort population, wherein the cut point value identifies a subject in the cohort population as positive or negative for a diagnostic test.

2. The method of claim 1, wherein the diagnostic feature metric is an expression score that is selected from the group consisting of an H-score, and Allred score, percent positivity, and an immunohistochemistry combination score.

3. The method of claim 1 wherein the diagnostic feature metric is a weighted combination of multiple image features or expression scores.

4. The method of claim 3, wherein the multiple image features or expression scores are pre-determined using a multivariate Cox model.

5. The method of claim 1, wherein the diagnostic feature metric is derived from a plurality of prognostic features, wherein the plurality of prognostic features are generated using a trained classifier.

6. The method of claim 5, wherein the plurality of prognostic features are combined using a multivariate Cox model for stratifying the cohort population.

7. The method of claim 1, wherein the statistical minimization method is a log rank statistic minimization.

8. The method of claim 1, wherein the subject outcome data is a primary end point data.

9. The method of claim 8, wherein the primary end point data is overall survival.

10. The method of claim 1, further comprising stratifying the subjects into diagnostic positive and diagnostic negative groups based on the determined cut point value.

11. The method of claim 10, further comprising generating Kaplan-Meier response curves of the diagnostic positive and diagnostic negative groups, wherein the Kaplan-Meier response curves indicate a percentage of subjects surviving over a period of time.

12. The method of claim 11, further comprising calculating hazard ratios based on a slope identified from the generated Kaplan-Meier response curves.

13. A system comprising:
one or more processors; and
a non-transitory computer-readable memory storing instructions which, when executed by the one or more processors, cause the one or more processors to:

access a plurality of images derived from biological samples of subjects in a cohort population, the biological samples having at least one stain;

compute, based on the plurality of image, a plurality of image features;

derive a diagnostic feature metric from the plurality of computed image features, wherein the plurality of computed image features are combined using a multivariate Cox model; and apply a statistical minimization to derive a cut point value that identifies a subject in the cohort population as positive or negative for a diagnostic test, the statistical minimization utilizing the derived diagnostic feature metric and subject outcome data.

14. The system of claim 13, wherein the plurality of computed image features to be combined are pre-determined.

15. The system of claim 13, wherein the plurality of computed image features to be combined are determined using a classifier trained to identify one or more attributes that are likely to predict a subject response.

16. The system of claim 13, wherein the cohort population is a placebo population.

17. The system of claim 13, wherein the statistical minimization is a log rank statistic minimization.

18. A non-transitory computer-readable storage medium encoded with instructions executable by a processor of a computing system to cause the computing system to:

access a plurality of images derived from biological samples of subjects in a cohort population, the biological samples having at least one stain;

compute, based on the plurality of images, a plurality of image features;

derive a diagnostic feature metric from the plurality of computed image features, wherein the plurality of computed image features are combined using a multivariate Cox model for stratifying the cohort population;

apply a log rank statistical minimization to derive a cut point value, the log rank statistical minimization utilizing the derived diagnostic feature metric and subject outcome data; and stratify the subjects in the cohort population into diagnostic positive and diagnostic negative groups based on the derived cut point value.

19. The non-transitory computer-readable storage medium of claim 18, further comprising instructions for generating Kaplan-Meier response curves.

20. The non-transitory computer-readable storage medium of claim 19, further comprising instructions for calculating hazard ratios based on the generated Kaplan-Meier response curves.

* * * * *